United States Patent
Dominguez et al.

(10) Patent No.: US 10,258,621 B2
(45) Date of Patent: Apr. 16, 2019

(54) METHODS AND COMPOSITIONS FOR TREATING HIV-RELATED DISORDERS

(71) Applicant: CHDI Foundation, Inc., New York, NY (US)

(72) Inventors: Celia Dominguez, Los Angeles, CA (US); Ignacio Muñoz-Sanjuán, Los Angeles, CA (US); Leticia Toledo-Sherman, Santa Monica, CA (US)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 15/326,317

(22) PCT Filed: Jul. 17, 2015

(86) PCT No.: PCT/US2015/040848
§ 371 (c)(1),
(2) Date: Jan. 13, 2017

(87) PCT Pub. No.: WO2016/011316
PCT Pub. Date: Jan. 21, 2016

(65) Prior Publication Data
US 2017/0209440 A1    Jul. 27, 2017

Related U.S. Application Data

(60) Provisional application No. 62/025,840, filed on Jul. 17, 2014.

(51) Int. Cl.
*C07D 239/42* (2006.01)
*A61K 31/52* (2006.01)
(Continued)

(52) U.S. Cl.
CPC ............ *A61K 31/505* (2013.01); *A61K 31/34* (2013.01); *A61K 31/506* (2013.01);
(Continued)

(58) Field of Classification Search
CPC ............................. A61K 31/505; A61K 31/52
(Continued)

(56) References Cited

U.S. PATENT DOCUMENTS 3,707,560 A    12/1972   De Angelis et al.
3,908,012 A    9/1975    De Angelis et al.
(Continued)

FOREIGN PATENT DOCUMENTS

CN    1566065    1/2005
EP    1679309    7/2006
(Continued)

OTHER PUBLICATIONS

Clercq "Anti-HIV drugs: 25 compounds approved within 25 years after the discovery of HIV," International Journal of Antimicrobial Agents, 2009, vol. 33, pp. 307-320.*
(Continued)

*Primary Examiner* — Shengjun Wang
(74) *Attorney, Agent, or Firm* — Sheppard Mullin Richter & Hampton LLP

(57) ABSTRACT

Certain adjunctive therapies comprising a kynurenine-3-monooxygenase inhibitor and an antiviral agent for treating HIV-related disorders are provided herein. These disorders include AIDS dementia complex, AIDS-induced encephalopathy, HIV-associated neurocognitive disorder, asymptomatic neurocognitive impairment, minor neurocognitive disorder, minor cognitive motor disorder, vacuolar myelopathy, peripheral neuropathies, and polymyositis. Also pro-
(Continued)

vided are pharmaceutical compositions comprising a kynurenine-3-monooxygenase inhibitor and an antiviral agent.

4 Claims, 11 Drawing Sheets

(51) Int. Cl.
  A61K 31/70    (2006.01)
  A61K 31/505   (2006.01)
  A61K 31/675   (2006.01)
  A61K 31/506   (2006.01)
  A61K 31/34    (2006.01)
  C07D 239/28   (2006.01)
  A61K 45/06    (2006.01)
(52) U.S. Cl.
  CPC ............ *A61K 31/675* (2013.01); *A61K 45/06* (2013.01); *C07D 239/28* (2013.01)
(58) Field of Classification Search
  USPC .......................................... 514/256, 263, 23
  See application file for complete search history.

(56) References Cited

U.S. PATENT DOCUMENTS

| | | | |
|---|---|---|---|
| 3,935,202 A | 1/1976 | Wei et al. |
| 3,950,525 A | 4/1976 | De Angelis et al. |
| 4,634,689 A | 1/1987 | Witkowski et al. |
| 4,824,846 A | 4/1989 | Kampe et al. |
| 4,920,119 A | 4/1990 | Attwood et al. |
| 4,931,443 A | 6/1990 | Nakao et al. |
| 5,064,832 A | 11/1991 | Stanek et al. |
| 5,102,904 A | 4/1992 | Venkataraman |
| 5,334,720 A | 8/1994 | Schmiesing et al. |
| 5,338,739 A | 8/1994 | Wettlaufer et al. |
| 5,439,912 A | 8/1995 | Hubele |
| 5,446,067 A | 8/1995 | Benoit et al. |
| 5,726,185 A | 3/1998 | Alig et al. |
| 5,925,639 A | 7/1999 | Doll et al. |
| 5,948,780 A | 9/1999 | Peterson et al. |
| 6,008,220 A | 12/1999 | Hupe et al. |
| 6,133,304 A | 10/2000 | Peterson et al. |
| 6,169,103 B1 | 1/2001 | Purchase et al. |
| 6,194,428 B1 | 2/2001 | Urbahns et al. |
| 6,211,214 B1 | 4/2001 | Kramer et al. |
| 6,214,822 B1 | 4/2001 | Treiber et al. |
| 6,239,288 B1 | 5/2001 | Purchase et al. |
| 6,248,765 B1 | 6/2001 | Schwartz et al. |
| 6,251,926 B1 | 6/2001 | Momose et al. |
| 6,288,063 B1 | 9/2001 | Kluender et al. |
| 6,340,709 B1 | 1/2002 | Bocan et al. |
| 6,399,612 B1 | 6/2002 | Purchase et al. |
| 6,455,520 B1 | 9/2002 | Brown et al. |
| 6,518,435 B1 | 2/2003 | Yamane et al. |
| 6,541,521 B1 | 4/2003 | Purchase et al. |
| 6,624,196 B2 | 9/2003 | Purchase et al. |
| 7,022,725 B2 | 4/2006 | Momose et al. |
| 7,049,318 B2 | 5/2006 | Dominguez et al. |
| 7,105,549 B2 | 9/2006 | Shao et al. |
| 7,345,178 B2 | 3/2008 | Nunes et al. |
| 7,947,680 B2 | 5/2011 | Jimenez et al. |
| 7,951,824 B2 | 5/2011 | Jaeschke et al. |
| 7,994,338 B2 | 8/2011 | Muchowski et al. |
| 8,071,631 B2 | 12/2011 | Muchowski et al. |
| 8,198,275 B2 | 6/2012 | Jimenez et al. |
| 8,536,186 B2 | 9/2013 | Wityak |
| 8,883,785 B2 | 11/2014 | Dominguez et al. |
| 9,145,373 B2 | 9/2015 | Wityak |
| 9,260,422 B2 | 2/2016 | Dominguez |
| 9,428,464 B2 | 8/2016 | Courtney et al. |
| 2002/0049207 A1 | 4/2002 | McCarthy |
| 2004/0077557 A1 | 4/2004 | Andreotti et al. |
| 2004/0204464 A1 | 10/2004 | Al-Abed |
| 2004/0214817 A1 | 10/2004 | Pierce et al. |
| 2004/0214888 A1 | 10/2004 | Matsuura et al. |
| 2005/0070584 A1 | 3/2005 | Havran et al. |
| 2005/0239854 A1 | 10/2005 | Sugiyama et al. |
| 2005/0288308 A1 | 12/2005 | Amrien et al. |
| 2006/0052606 A1 | 3/2006 | Liebeschuetz et al. |
| 2006/0178388 A1 | 8/2006 | Wrobleski et al. |
| 2006/0189806 A1 | 8/2006 | Bernardini et al. |
| 2006/0223849 A1 | 10/2006 | Mjalli et al. |
| 2006/0252751 A1 | 11/2006 | Xue et al. |
| 2006/0252764 A1 | 11/2006 | Guillemont et al. |
| 2006/0293339 A1 | 12/2006 | Chakravarty et al. |
| 2007/0060573 A1 | 3/2007 | Wortmann et al. |
| 2007/0275950 A1 | 11/2007 | Miyata et al. |
| 2008/0019915 A1 | 1/2008 | Hadida-Ruah et al. |
| 2008/0058391 A1 | 3/2008 | Johnson et al. |
| 2008/0070937 A1 | 3/2008 | Muchowski et al. |
| 2008/0077419 A1 | 3/2008 | Santiago et al. |
| 2008/0113997 A1 | 5/2008 | Sielecki-Dzurdz et al. |
| 2008/0187575 A1 | 8/2008 | Kiebl et al. |
| 2008/0188452 A1 | 8/2008 | Altenbach et al. |
| 2009/0036428 A1 | 2/2009 | Kawakami et al. |
| 2009/0270405 A1 | 10/2009 | Cook et al. |
| 2010/0022546 A1 | 1/2010 | Jimenez et al. |
| 2010/0101643 A1 | 4/2010 | Takahashi et al. |
| 2010/0152178 A1 | 7/2010 | Osakada et al. |
| 2011/0015232 A1 | 1/2011 | Charest et al. |
| 2011/0178086 A1 | 7/2011 | Jimenez et al. |
| 2011/0183957 A1* | 7/2011 | Wityak ................ C07D 213/79 514/210.2 |
| 2011/0230428 A1 | 9/2011 | Wityak et al. |
| 2012/0041009 A1 | 2/2012 | Mizuno |
| 2012/0329812 A1 | 12/2012 | Wityak et al. |
| 2013/0029988 A1 | 1/2013 | Dominguez et al. |
| 2013/0116216 A1 | 5/2013 | Dominguez et al. |
| 2013/0331370 A1 | 12/2013 | Wityak et al. |
| 2014/0329795 A1 | 11/2014 | Courtney et al. |
| 2014/0329816 A1 | 11/2014 | Dominguez et al. |
| 2015/0057238 A1 | 2/2015 | Toledo-Sherman et al. |
| 2016/0251318 A1 | 9/2016 | Courtney et al. |
| 2016/0257674 A1 | 9/2016 | Dominguez et al. |
| 2016/0272611 A1 | 9/2016 | Dominguez et al. |

FOREIGN PATENT DOCUMENTS

| | | |
|---|---|---|
| EP | 1783116 | 5/2007 |
| EP | 1928842 | 6/2008 |
| EP | 2090570 | 8/2009 |
| EP | 2338887 | 6/2011 |
| FR | 2204406 | 5/1974 |
| JP | 01113377 | 5/1989 |
| JP | 07041459 | 2/1995 |
| JP | 2000198771 | 7/2000 |
| JP | 2002241358 | 8/2002 |
| JP | 2007-230963 | 9/2007 |
| JP | 2009-280521 | 12/2009 |
| WO | WO 95/23135 | 8/1995 |
| WO | WO 98/37079 A1 | 8/1998 |
| WO | WO 99/21583 | 5/1999 |
| WO | WO 01/34579 | 5/2001 |
| WO | WO 01/60781 | 8/2001 |
| WO | WO 2001/89457 | 11/2001 |
| WO | WO 02/060877 | 8/2002 |
| WO | WO 2002/085891 | 10/2002 |
| WO | WO 03/002536 | 1/2003 |
| WO | WO 03/022276 A1 | 3/2003 |
| WO | WO 03/029210 | 4/2003 |
| WO | WO 03/051833 | 6/2003 |
| WO | WO 03/066623 A1 | 8/2003 |
| WO | WO 2004/014844 A2 | 2/2004 |
| WO | WO 2004/026833 | 4/2004 |
| WO | WO 2004/032933 A1 | 4/2004 |
| WO | WO 2004/058762 A1 | 7/2004 |
| WO | WO 2004/108686 | 12/2004 |
| WO | WO 2005/003123 A1 | 1/2005 |
| WO | WO 2005/037793 A1 | 4/2005 |
| WO | WO 2005/042498 A2 | 5/2005 |
| WO | WO 2005/079800 | 9/2005 |

(56) References Cited

FOREIGN PATENT DOCUMENTS

| | | |
|---|---|---|
| WO | WO 2005/079801 | 9/2005 |
| WO | WO 2005/079802 | 9/2005 |
| WO | WO 2005/095400 A1 | 10/2005 |
| WO | WO 2006/000371 | 1/2006 |
| WO | WO 2006/039718 | 4/2006 |
| WO | WO 2006/051270 | 5/2006 |
| WO | WO 2006/062093 A1 | 6/2006 |
| WO | WO 2006/086600 A1 | 8/2006 |
| WO | WO 2006/133333 | 12/2006 |
| WO | WO 2007/017289 A2 | 2/2007 |
| WO | WO 2007/019416 A1 | 2/2007 |
| WO | WO 2007/024922 A1 | 3/2007 |
| WO | WO 2007/039470 | 4/2007 |
| WO | WO 2007/067836 A2 | 6/2007 |
| WO | WO 2007/070818 A1 | 6/2007 |
| WO | WO 2007/087637 | 8/2007 |
| WO | WO 2007/093542 | 8/2007 |
| WO | WO 2007/096072 | 8/2007 |
| WO | WO 2007/097403 | 8/2007 |
| WO | WO 2008/002576 A2 | 1/2008 |
| WO | WO 2008/009963 | 1/2008 |
| WO | WO 2008/022281 | 2/2008 |
| WO | WO 2008/022286 | 2/2008 |
| WO | WO 2008/023720 A1 | 2/2008 |
| WO | WO 2008/034008 A2 | 3/2008 |
| WO | WO 2008/095852 A1 | 8/2008 |
| WO | WO 2008/121877 A2 | 10/2008 |
| WO | WO 2008/152099 A2 | 12/2008 |
| WO | WO 2009/006389 | 1/2009 |
| WO | WO 2009/082346 A1 | 7/2009 |
| WO | WO 2009/148004 A1 | 12/2009 |
| WO | WO 2010/005783 A1 | 1/2010 |
| WO | WO 2010/017179 | 2/2010 |
| WO | WO 2010/020432 | 2/2010 |
| WO | WO 2010/044404 | 4/2010 |
| WO | WO 2010/045188 | 4/2010 |
| WO | WO 2010/052448 | 5/2010 |
| WO | WO 2010/055077 | 5/2010 |
| WO | WO 2010/079443 | 7/2010 |
| WO | WO 2010/100475 A1 | 9/2010 |
| WO | WO 2010/117323 | 10/2010 |
| WO | WO 2010/125402 | 11/2010 |
| WO | WO 2010/134478 A1 | 11/2010 |
| WO | WO 2011/008709 | 1/2011 |
| WO | WO 2011/043568 | 4/2011 |
| WO | WO 2011/046771 A1 | 4/2011 |
| WO | WO 2011/050323 A1 | 4/2011 |
| WO | WO 2011/091153 | 7/2011 |
| WO | WO 2011/104322 A1 | 9/2011 |
| WO | WO 2012/003387 A1 | 1/2012 |
| WO | WO 2012/035421 A2 | 3/2012 |
| WO | WO 2012/078777 | 6/2012 |
| WO | WO 2013/016488 A1 | 1/2013 |
| WO | WO 2013/033068 | 3/2013 |
| WO | WO 2013/033085 | 3/2013 |
| WO | WO 2013/151707 | 10/2013 |

OTHER PUBLICATIONS

International Search Report and Written Opinion of PCT/US2015/040848 dated Oct. 23, 2015 (18 pages).
Allen, "Pyrolysis of oximes of some y-cyano and y-nitro ketones," Canadian Journal of Chemistry (1965), 43(9), 2486-92.
Arzel, et al. A new synthesis of a-substituted 6-carbolines. Journal of Heterocyclic Chemistry vol. 34, Issue 4, pp. 1205-1210, 1997.
Banker "Modern Pharmaceutics" 3rd Edition. p. 451, 596 (2002).
Berthel, et al., "Identification of phenyl-pyridine-2-carboxylic acid derivatives as novel cell cycle inhibitors with increased selectivity for cancer cells." Anti-Cancer Drugs, 13:359-366 (2002).
Blomquist et al., "Many-membered carbon rings. XVII. A paracyclophane possessing two gem-dimethyl groups," Journal of the American Chemical Society (1958), 80, 3405-8.
Bredereck, et al., "Foramid-Reaktionen, VIII. Eine neue pyrimidin-synthese." Chemische Berichte 90:942-52 (1957).
Brinkmann et al., Fingolimod (FTY720): discovery and development of an oral drug to treat multiple sclerosis. Nat Rev Drug Discov. Nov. 2010;9(11):883-97. doi: 10.1038/nrd3248. Epub Oct. 29, 2010.
Brown et al., "Product class 16: benzisothiazoles," Science of Synthesis (2002), 11, 573-625.
Bundgaard, Design of Prodrugs, Elsevier, 1985.
Chatterjea, et al., "Synthesis in 3-azafluorene group. Part III." J. Indian Chem. Soc., vol. LXI, 1028-1031 (1984).
Chemcast RN 1261956-00-6 (2016).
Chemical Abstracts Service. CAS Reg. No. 1017484-83-1 (Apr. 27, 2008).
Chemical Abstracts Service. CAS Reg. No. 1017484-87-5 (Apr. 27, 2008).
Chemical Abstracts Service. CAS Reg. No. 1017484-91-1 (Apr. 27, 2008).
Chemical Abstracts Service. CAS Reg. No. 1017484-95-5 (Apr. 27, 2008).
Chemical Abstracts Service. CAS Reg. No. 52565-56-7 (1984), 1p.
Chemical Abstracts Service. CAS Reg. No. 55240-51-2 (1984), 1 p.
Chemical Abstracts Service. CAS Reg. No. 887407-77-4 (2006), 1 p.
Chemical Abstracts Service. CAS Reg. No. 1017394-18-1 (Apr. 25, 2008).
Chemical Abstracts Service. CAS Reg. No. 1017396-21-2 (Apr. 25, 2008).
Chemical Abstracts Service. CAS Reg. No. 1017396-26-7 (Apr. 25, 2008).
Chemical Abstracts Service. CAS Reg. No. 1017396-31-4 (Apr. 25, 2008).
Chemical Abstracts Service. CAS Reg. No. 1017438-20-8 (Apr. 25, 2008).
Chemical Abstracts Service. CAS Reg. No. 1017438-24-2 (Apr. 25, 2008).
Chemical Abstracts Service. CAS Reg. No. 1017438-28-6 (Apr. 25, 2008).
Chemical Abstracts Service. CAS Reg. No. 1017438-32-2 (Apr. 25, 2008).
Chemical Abstracts Service. CAS Reg. No. 1017438-36-6 (Apr. 25, 2008).
Chemical Abstracts Service. CAS Reg. No. 1017484-79-5 (Apr. 27, 2008).
Chemical Abstracts Service. CAS Reg. No. 1017484-99-9 (Apr. 27, 2008).
Chemical entity, Wikipedia, p. 1-2 (2017).
Chen et al. "Pyrimidine . . . " CA150:121675 (2009).
Chiarugi et al. Similarities and differences in the neuronal death processes activated by 3OH-kynurenine and quinolinic acid. J. Neurochem. 2001, 77, 1310-1318.
Child et al., "Fenbufen, a new anti-inflammatory analgesic: synthesis and structure-activity relations of analogs," Journal of Pharmaceutical Sciences (1977), 66(4), 466-76.
Clapham et al., Trifluoromethyl-substituted pyridyl- and pyrazolylboronic acids and esters: synthesis and Suzuki-Miyaura cross-coupling reactions, Organic & Biomolecular Chemistry, 7(10), pp. 2155-2161 (2009).
Collins, et al. Design and development of signal transduction inhibitors for cancer treatment: experience and challenges with kinase targets. Current Signal Transduction Therapy, 1(1):13-23(11) (2006).
Connor et al., Induction of indolamine 2,3-dioxygenase and kynurenine 3-monooxygenase in rat brain following a systemic inflammatory challenge: a role for IFN-gamma? Neurosci Lett. Aug. 15, 2008;441(1):29-34. doi: 10.1016/j.neulet.2008.06.007. Epub Jun. 7, 2008.
Courtney, et al. "Modulation of the Kynurenine Pahway for the Potential Treatment of Neurodegenerative Diseases." Top Med. Chem. V. 6, p. 149-176 (2010).
Dalal et al. "Substituted Butyro Lactones. Part III. Synthesis of γ-(4-alkoxy-3-chlorophenyl)butyrolactones." J. Ind. Chem. 1958, 35, 742.
Damasio, Alzheimer's Disease and Related Dementias, Cecil Textbook of Medicine, 20th Edition, vol. 2, pp. 1992-1996, 1996.

(56) References Cited

OTHER PUBLICATIONS

Database Registry, Chemical Library Supplier: Ambinte, Entered STN: 25, Apr. 2008. (RN No. 1017438-16-2).
Douglas, Jr. Introduction to Viral Diseases, Cecil Textbook of Medicine, 20th Edition, vol. 2, pp. 1739-1747, 1996.
Dounay, et al. Challenges and Opportunities in the Discovery of New Therapeutics Targeting the Kynurenine Pathway. J Med Chem. Nov. 25, 2015;58(22):8762-82. doi: 10.1021/acs.jmedchem. 5b00461. Epub Aug. 5, 2015.
Eglinton, et al., "The chemistry of fungi. Part XXXV. A preliminary investigation of ergoflavin." View Online/Journal Homepage, 1833-1842 (1958).
EP Application No. 09805426. Suppl. Search Report dated Feb. 2, 2012.
Filosa, et al., "Synthesis and antiproliferative properties of N3/8-disubstituted 3,8-diazabicyclo[3.2.1]octane analogues of 3,8-bis[2-(3,4,5-trimethoxphenyl)pyridine-4-yl]methyl-piperazine." Eur. J. Med. Chem. 42:293-306 (2007).
Fotsch et al. "Preparation of pyridylmethyl . . . " CA152:476968 (2010).
Furuya et al. "Cyanuric Chloride as a Mild and Active Beckmann Rearrangement Catalyst ," Journal of the American Chemical Society (2005), 127(32), 11240-11241.
Gillespie et al. "Preparation of pyrimidine . . . " CA143:248409 (2005).
Giorgini et al. A genomic screen in yeast implicates kynurenine 3-monooxygenase as a therapeutic target for Huntington disease. Nat Genet. May 2005;37(5):526-31. Epub Apr. 3, 2005.
Girouard et al., Neurovascular coupling in the normal brain and in hypertension, stroke, and Alzheimer disease. J Appl Physiol (1985). Jan. 2006;100(1):328-35.
Goldfarb, CAPLUS Abstract 151:92839 (2009).
Gregoire et al., Prolonged kynurenine 3-hydroxylase inhibition reduces development of levodopa-induced dyskinesias in parkinsonian monkeys. Behav Brain Res. Jan. 25, 2008;186(2):161-7. Epub Aug. 10, 2007.
Gura et al., Systems for identifying new drugs are often faulty, Science, 278:1041-1042, 1997.
Hametner et al., CAPLUS Abstract 135:241866 (2001).
Han, et al., "Lead optimization studies on FimH antagonists: discovery of potent and orally bioavailable ortho-substituted biphenyl mannosides." J. Med. Chem. 55:3945-3959 (2012).
Hassner et al., "Cycloadditions. 43. Stereospecific synthesis of functionalized Cyclopentanes," Tetrahedron Letters (1989), 30(42), 5803-6.
Hoffman et al., CAPLUS Abstract 117:7954 (1992).
Hurst et al., Intramolecular Diels-Alder reactions of α, β-unsaturated oxime ethers as 1-azadienes: synthesis of [c]-fused pyridines, ScienceDirect, Tetrahedron vol. 64 ,pp. 874-882, (2008).
Imoto et al. "Studies on non-thiazolidinedione antidiabetic agents. 2. Novel oxyiminoalkanoic acid derivatives as potent glucose and lipid lowering agents," Chemical & Pharmaceutical Bulletin (2003), 51(2), 138-151.
Improper Markush, Fed. Reg. v. 76(27) 7162-7175, slides 64-67 (2011).
International Preliminary Report on Patentability along with Written Opinion of the International Searching Authority for PCT/US2012/52648 dated Nov. 2, 2012 (9 pages).
International Preliminary Report on Patentability dated Jul. 31, 2012 for PCT/US2011/021890. (6 pages).
International Preliminary Report on Patentability, PCT/US2009/052667 (dated Feb. 8, 2011).
International Search Report & Written Opinion dated Oct. 13, 2009 for PCT/US2009/052667. 7 pages.
International Search Report & Written Opinion dated Oct. 22, 2012 for PCT/US2012/052617. 8 pages.
International Search Report & Written Opinion dated Sep. 24, 2012 for PCT/US2012/48254. 8 pages.
International Search Report and Written Opinion dated Sep. 29, 2009 for PCT/US2009/052560, 8 pages.
International Search Report dated Mar. 29, 2011 for PCT/US2011/021890. 3 pages.
International Search Report dated Nov. 2, 2012 for PCT/US2012/052648. 3 pages.
Johnson et al., Relationships between drug activity in NCI preclinical in vitro and in vivo models and early clinical trials, British Journal of Cancer, 84(10):1424-1431,2001.
Kato et al. CAPLUS Abstract 73:77194 (1970).
Kato et al., "The Vilsmeier reaction of methylpyrimidine derivatives." Yakugaku Zasshi 90(7):870-876 (1970).
Kawamoto et al. "Preparation of biarylamide . . . " CA146:401963 (2007).
Kemp et al., "N-Ethylbenzisoxazolium cation. I. Preparation and reactions with nucleophilic species," Tetrahedron (1965), 21(11), 3019-35.
Khachatryan et al. "Synthesis and heterocyclization of b-aroyl-a-diphenyl-phosphorylpropionic acids," Chemistry of Heterocyclic Compounds (New York, NY, United States) (Translation of Khimiya Geterotsiklicheskikh Soedinenii) (2004), 40(4), 446-451.
Khachikyan et al. "Reaction of b-Aroylacrylic Acids with Triphenylphosphine Hydrobromide and Certain Reactions of the Resulting Products," Russian Journal of General Chemistry (2005), 75(12), 1895-1898.
Kobayashi, et al., "A novel strategy for the synthesis of 2-arylpyridines using one-pot 6 Π-azaelectrocyclization." Tetrahedron Ltrs., 49:4349-4351 (2008).
Kohler et al., "Isoxazoline oxides," Journal of the American Chemical Society (1926), 48, 2425-34.
Kort, et al., "Subtype-selective Nav1.8 sodium channel blockers: Identification of potent orally active nicotinamide derivatives." Bioorg. & Med. Chem. Ltrs. 20:6812-6815 (2010).
Kulkarni, et al., "Design and synthesis of novel heterobiaryl amides as metabotropic glutamate receptor subtype 5 antagonists." Bioorg. & Med. Chem. Ltrs. 17:2074-2079 (2007).
Lafferty et al. "The preparation and properties of certain pyridylpyrimidines and bidiazines as potential chelating agents for Iron(II)" J. Org. Chem. 1967, 32, 1591-1596.
Layzer, Degenerative Diseases of the Nervous System, Cecil Textbook of Medicine, 20th Edition, vol. 2, pp. 2050-2057, 1996.
Levin at al., Europium Catalyzed Intramolecular Oxazole Diels-Alder Reactions for the Synthesis of Benzopyrano [4,3-b]Pyridines and Benzo [h]-1,6-Naphthyridines, Tetrahedron Letters, vol. 30, No. 18, pp. 2355-2358 (1989).
LeWitt. Levodopa for the Treatment of Parkinson's Disease. N Engl J Med. Dec. 4, 2008;359(23):2468-76. doi: 10.1056/NEJMct0800326.
Li, et al., "Discovering novel chemical inhibitors of human cyclophilin A: virtual screening, synthesis, and bioassay." Bioorganic & Medicinal Chemistry, 14:2209-2224 (2006).
Machado-Alba, et al. Effectiveness of antiretroviral treatment in Colombia. Rev. Panam. Salud. Publica. 2012; 32(5):360-367.
Masaki et al., "Dehydration of 4-oximinocarboxylic acids with dicyclohexylcarbodiimide," Journal of Heterocyclic Chemistry (1965), 2(4), 376-8.
Mason et al., "Some Aryl Substituted 2-(4-Nitrophenyl)-4-oxo-4-phenylbutanoates and 3-(4-Nitrophenyl)-1-phenyl-1,4-butanediols and Related Compounds as Inhibitors of Rat Liver Microsomal Retinoic Acid Metabolising Enzymes," Journal of Enzyme Inhibition and Medicinal Chemistry (2003), 18(6), 511-528.
Maurin et al., "Structure of (E)-4-benzoylbutyramide oxime," Acta Crystallographica, Section C: Crystal Structure Communications (1992), C48(10), 1819-20.
Maurin et al., "Structures of 4-hydroxyimino-4-phenylbutanoic acid, C10H11NO3 (I), and 5-hydroxyimino-5-phenylpentanoic acid, C11H13NO3 (II), at 223 K," Acta Crystallographica, Section C: Crystal Structure Communications (1994), C50(1), 78-81.
McKinnon et al., "Fused heterocycles from o-acylbenzenethiol derivatives," Canadian Journal of Chemistry (1988), 66(6), 1405-9.
Migliara et al., "A new route for the preparation of pyrazolo[3,4-c]pyridines," Journal of Heterocyclic Chemistry (1979), 16(3), 577-9.
Migliara et al., "Synthesis of 1-hydroxy-2,4-diphenylpyrrolo[2,3-d]pyridazin-7(6H)-one," Journal of Heterocyclic Chemistry (1979), 16(1), 203.

(56) References Cited

OTHER PUBLICATIONS

Mikhaleva et al., CAPLUS Abstract 91:107951 (1979).
Mitchell et al., Amyotrophic lateral sclerosis. Lancet. Jun. 16, 2007;369(9578):2031-41.
Molina et al;, Unusual Reactivity of (Vinylimino) phosphoranes and Their Utility in the Preparation of Pyridine and Dihydropyridine Derivatives, J. Organic Chemistry, vol. 61 , pp. 8094-8098, (1996).
Molina, et al., "Electrocylization of 3-azahexa-1,3,5-trienes: a convenient iminophosphorane-mediated preparation of 4-arylpyridines." Tetrahedron Ltrs. 34(23):3773-3776 (1993).
Molyneux, "The resorcinol-maleic anhydride condensation product. An unequivocal proof of structure," Journal of Organic Chemistry (1978), 43(13), 2730-1.
Nerurkar et al., "b-Arylglutaconic acids. IV. Synthesis of crotono- and valerolactones of b-arylglutaconic and glutaric acids," Journal of Organic Chemistry (1960), 25, 1491-5.
Oare et al., "Acyclic stereoselection. 46. Stereochemistry of the Michael addition of N,N-disubstituted amide and thioamide enolates to a,b-unsaturated ketones," Journal of Organic Chemistry (1990), 55(1), 132-57.
O'Brien et al., Vascular cognitive impairment. The Lancet, Neurology. Feb. 2003; 2(2):89-98.
Osborne et al., "The chemistry of triazine derivatives II. The acylation of 2,4,6-trimethyl-s-triazine to triazinyl ketones and their facile isomerization to acetamidopyrimidines." J. Heterocyclic Chem. 1 (Jul. 1, 1964) pp. 145-150 (1964).
Overmars et al., "Fluvoxamine maleate: metabolism in man," European Journal of Drug Metabolism and Pharmacokinetics (1983), 8(3), 269-80.
Papet et al., CAPLUS Abstract 119:271098 (1993).
Patani et al. "Bioisosterism: a rational approach in drug design" Chem Rev. 96, 3147-3176 (1996).
Pearce et al., Failure modes in anticancer drug discovery and development, Cancer Drug Design and Discovery Edited by Stephen Neidle, Chapter 18, pp. 424-435 (2008).
Pimentel and McClellan, The Hydrogen Bond, Freeman, San Francisco, 1960.
Poupaert, Drug Design: Basic Principles and Applications, in 2 Encyclopedia of Pharmaceutical Technology 1362-1369, 1367 (James Swarbrick ed., 3rd ed., 2007).
Pratsch, et al., "Hydroxy- and aminophenyl radicals from arenediazonium salts." Chem. Eur. J. 17:4104-4108 (2011).
Proctor, et al., "Bridged-ring nitrogen compounds. part 5,1 synthesis of 2,6-methano-3-benzazonine ring-systems." JCS Perkin I, 1754-1762 (1981).
Sakaguchi, et al., "Library-directed solution- and solid-phase synthesis of 2,4-disubstituted pyridines: one-pot approach through 6 Π-azaelectrocyclization." Chem. Asian. J. 4:1573-1577 (2009).
Sakamoto, et al. "Studies on pyrimidine derivatives. XV. Homolytic acylation and amidation of simply substituted pyrimidines." Chem. Pharm. Bull. 1980, 28, 202-207.
Sakamoto, et al., "Studies on pyrimidine derivatives. XVI. site selectivity in the homolytic substitution of simple pyrimidines." Chem. Pharm. Bull. 1980, 28, 571-577.
Saravanan et al., "Tandem Ring Opening and Oximation of Ethyl 3-Aroyl-1-cyano-4-hydroxy-2,4,6-triarylcyclohexanecarboxylate by Hydroxylamine," Synthetic Communications (2007), 37(20), 3635-3648.
Sasse et al. "New Histamine H3-Receptor Ligands of the Proxifan Series: Imoproxifan and Other Selective Antagonists with High Oral in Vivo Potency," Journal of Medicinal Chemistry (2000), 43(17), 3335-3343.
Sathyasaikumar et al., Dysfunctional Kynurenine Pathway Metabolism in the R6/2 Mouse Model of Huntington's Disease, J Neurochem. 113(6), pp. 1416-1425, Jun. 2010.
Savarin et al. "Novel Intramolecular Reactivity of Oximes: Synthesis of Cyclic and Spiro-Fused Imines," Organic Letters (2007), 9(6), 981-983.
Saygili et al., CAPLUS Abstract 141:7086 (2004).
Schilt et al., CAPLUS Abstract 85:186182 (2 pages) (1976).
Schwarcz et al., Kynurenines in the mammalian brain: when physiologu meets pathology. Nat Rev Neurosci. Jul. 2012;13(7):465-77. doi: 10.1038/nrn3257.
Shah et al., Current approaches in the treatment of Alzheimer's disease. Biomed Pharmacother. Apr.-May 2008;62(4):199-207. doi: 10.1016/j.biopha.2008.02.005. Epub Mar. 17, 2008.
Shao, et al., Phenoxyphenyl pyridines as novel state-dependent, high-potency sodium channel inhibitors. J. Med. Chem. 47:4277-4285 (2004).
Silverman, Prodrugs and Drug Delivery Systems, The Organic Chemistry of Drug Design and Drug action, Chapter 8, pp. 352-400, 1992.
Simone, Oncology: Introduction, Cecil Textbook of Medicine, 20th Edition, vol. 1, pp. 1004-1010, 1995.
Stevens et al., "Chemistry and structure of mitomycin C," Journal of Medicinal Chemistry (1965), 8(1), 1-10.
Stone, et al. Kynurenine pathway inhibition as a therapeutic strategy for neuroprotection. FEBS J. Apr. 2012;279(8):1386-97. doi: 10.1111/j.1742-4658.2012.08487.x. Epub Mar. 27, 2012.
Tanimoto et al., "Synthesis of 6-alkoxy-3-aryl-6-(trimethylsilyloxy)-5,6-dihydro-4H-1,2-oxazines and their acid catalyzed hydrolysis leading to 3-aryl-5,6-dihydro-4H-1,2-oxazin-6-ones and (or) 4-aryl-4- (hydroxyimino)butyric acid esters," Journal of the Chemical Society, Perkin Transactions 1: Organic and Bio-Organic Chemistry (1972-1999) (1991), (12), 3153-7.
Testa, et al. Prodrug Design in, 5 Encyclopedia of Pharmaceutical Technology, 3008-3014 (J. Swarbrick ed., 3rd Ed. 2007).
Tomoeda et al., "A synthesis of 5-benzyl-2-pyrrolidinone," Yakugaku Zasshi (1966), 86(12), 1213-16.
Van Der Zanden et al., "Action of BF3-ether upon methylchavicol, the oximes of g-p-methoxy- and g-p-ethoxybenzoylbutyric acids and the oxime of benzophenone," Recueil des Travaux Chimiques des Pays-Bas et de la Belgique (1942), 61, 280-4.
Van Der Zanden et al., "Reduction products of g-anisoylbutyric acid, its oxime and the ethoxy homologs," Recueil des Travaux Chimiques des Pays-Bas et de la Belgique (1942), 61, 365-72.
Van Der Zanden, et al., "Polymers of methylchavicol. 1,5-Dianisyl-4-methyl-1-pentene," Recueil des Travaux Chimiques des Pays-Bas et de la Belgique (1943), 62, 383-92.
Van Muijlwijk-Koezen, et al., "Thiazole and thiadiazole analogues as a novel class of adenosine receptor antagonists." J. Med. Chem. 44:749-762 (2001).
Von Angerer, "Product class 12: pyrimidines." Science of Synthesis Houben-Weyl Methods of Molecular Transformations, Category 2, vol. 16 (2003).
Warshakoon, et al., "Design and synthesis of substituted pyridine derivatives as HIF-1α prolyl hydroxylase inhibitors." Bioorganic & Medicinal Chemistry Lett. 16:5616-5620 (2006).
Wienhoefer et al., CAPLUS Abstract 81 :169509 (1974).
Wilkerson et al. (Eur. J. Med. Chem., 1992, 27(6), 595).
Wolff "Burger's Medicinal Chemistry and Drug Discovery." p. 975-977 (1995).
Wonodi, et al. Downregulated kynurenine 3-monooxygenase gene expression and enzyme activity in schizophrenia and genetic association with schizophrenia endophenotypes. Arch Gen Psychiatry. Jul. 2011;68(7):665-74. doi: 10.1001/archgenpsychiatry.2011.71.
Written Opinion of the International Search Authority for PCT/US2009/004244, dated Jan. 22, 2011.
Zon et al., In vivo drug discovery in the zebrafish. Nat Rev Drug Discov. Jan. 2005;4(1):35-44.
Toledo-Sherman et al., "Development of a Series of Aryl Pyrimidine Kynurenine Monooxygenase Inhibitors as Potential Therapeutic Agents for the Treatment of Huntington's Disease," J. Med. Chem., 58, pp. 1159-1183 (2015).

* cited by examiner

METHODS AND COMPOSITIONS FOR TREATING HIV-RELATED DISORDERS

CROSS REFERENCE TO RELATED APPLICATIONS

This application is a U.S. National Stage Application under 35 U.S.C. § 371 of PCT Application No. PCT/US2015/040848, filed Jul. 17, 2015, which claims the benefit of U.S. Provisional Appln. No. 62/025,840, filed Jul. 17, 2014, which is incorporated herein by reference for all purposes.

This application claims the benefit of U.S. Provisional Appln. No. 62/025,840, filed Jul. 17, 2014, which is incorporated herein by reference for all purposes.

Provided herein are certain adjunctive therapies for HIV-related disorders comprising administering a kynurenine-3-monooxygenase inhibitor with an antiviral agent. Also provided herein are pharmaceutical compositions comprising a kynurenine-3-monooxygenase inhibitor and an antiviral agent.

Inflammatory processes contribute significantly to the progression and manifestations of a broad spectrum of central nervous system (CNS) diseases, including acute and chronic microbial infections, autoimmune processes, stroke, and physical trauma to the CNS. There are many mechanisms by which inflammation could cause neurological disease, including the production of neurotoxic agents by the host or invading microbes. Identification of such mediators and the processes that lead to their production and accumulation are important steps in developing rational approaches to therapy. Motor abnormalities, cognitive deficits, and dementia (encephalopathy) are frequent complications of infection with the human immunodeficiency virus (HIV) and can occur independently of opportunistic CNS infections. The most frequent neuropathologic substrate associated with neurological symptoms is HIV encephalitis, an inflammatory condition characterized by the presence of HIV-infected macrophages, astrogliosis, white matter pallor, and neuronal injury (loss of neurons and synapses). The production of toxins by microglia/macrophages has been hypothesized as a possible mechanism responsible for neurological dysfunction and neurodegeneration, because HIV is localized predominantly in microglia/macrophages and because macrophage-tropic isolates are associated with neurological disease to a greater extent than T cell tropic isolates. Potential host-coded neurotoxins include the NMDA receptor agonist quinolinic acid (QUIN).

QUIN is an excitotoxic metabolite of the tryptophan-kynurenine pathway. In models of inflammatory neurological disorders such as experimental allergic encephalitis, bacterial and viral infections, forebrain global ischemia or spinal trauma, brain QUIN levels are extremely elevated. This increased brain QUIN concentration could be due to either an elevated circulating concentration of the excitotoxin or to an increased de novo synthesis in activated microglia or in infiltrating macrophages. QUIN is an agonist of a subgroup of NMDA receptors and when directly injected into brain areas it destroys most neuronal cell bodies sparing fibers en passant and neuronal terminals. QUIN is a relatively poor agonist of the NMDA receptor complex containing either NR2C or NR2D subunits, while it interacts with higher affinity with the NR2A subunit (7-10 µmol) and the NR2B subunit (100 µmol). In vitro, the neurotoxic effects of the compound have been studied in different model systems with variable results: chronic exposure of organotypic cortico-striatal cultures to submicromolar concentration of QUIN causes histological signs of pathology; similar results have been obtained after chronic exposure of cultured neuronal cells.

Sustained increases in the concentrations of QUIN occur in cerebral spinal fluid (CSF) and blood of HIV-infected patients and macaques infected with the simian immunodeficiency virus (SIV), and begin soon after primary infection. Elevated CSF QUIN is associated with motor deficits and virus recovery from the CNS in the early asymptomatic stages of disease, and correlate with quantitative measures of neuropsychologic deficits, striatal and limbic atrophy, and markers of intrathecal immune activation (CSF $\beta_2$-microglobulin and neopterin concentrations) in late stage patients. One study reported that in HIV-infected patients, brain QUIN concentrations were elevated by >300-fold, to concentrations that exceeded cerebrospinal fluid (CSF) by 8.9-fold. Furthermore, in retrovirus-infected macaques, the largest kynurenine pathway responses in brain and CSF were associated with retrovirus-induced encephalitis. Direct measures of the amount of QUIN in brain derived from blood in a macaque with encephalitis showed that almost all QUIN (98%) was synthesized locally within the brain. In contrast to the brain changes, there was no difference in any systemic measure between macaques with encephalitis and those without. These results demonstrate a role for induction of indoleamine-2,3-dioxygenase (IDO) in accelerating the local formation of QUIN within the brain tissue, particularly in areas of encephalitis, rather than entry of QUIN into the brain from the meninges or blood. In fact, robust increases in the activities of IDO, and two other enzymes in the kynurenine pathway of tryptophan metabolism, kynurenine-3-monooxygenase (KMO) and kynureninase (KYNU) have been found in areas of brain inflammation. Accordingly, strategies to reduce QUIN production, targeted at intracerebral sites, are potential approaches to therapy.

The pathogenesis of human and simian immunodeficiency viruses is characterized by CD4(+) T cell depletion and chronic T cell activation, leading ultimately to AIDS. CD4(+) T helper (T(H)) cells provide protective immunity and immune regulation through different immune cell functional subsets, including T(H)1, T(H)2, T regulatory (T(reg)), and interleukin-17 (IL-17)-secreting T(H)17 cells. Because IL-17 can enhance host defenses against microbial agents, thus maintaining the integrity of the mucosal barrier, loss of T(H)17 cells may foster microbial translocation and sustained inflammation. It has been found that in HIV-seropositive subjects progressive disease is associated with the loss of T(H)17 cells and a reciprocal increase in the fraction of the immunosuppressive T(reg) cells both in peripheral blood and in rectosigmoid biopsies. The loss of T(H)17/T(reg) balance is associated with induction of indoleamine-2,3-dioxygenase 1 (IDO1) by myeloid antigen-presenting dendritic cells and with increased plasma concentration of microbial products. In vitro, the loss of T(H) 17/T(reg) balance is mediated directly by the proximal tryptophan catabolite from IDO metabolism, 3-hydroxyanthranilic acid (3-OH-AA). It has been postulated that induction of IDO may represent a critical initiating event that results in inversion of the T(H)17/T(reg) balance and in the consequent maintenance of a chronic inflammatory state in progressive HIV disease. Accordingly, strategies to lower 3-OH-AA levels are predicted to eliminate or ameliorate systemic inflammation after HIV infection.

KMO catalyzes the conversion of kynurenine (KYN) into 3-hydroxykynurenine (3-HK or 3-OH—KYN), which is further degraded by KYNU to 3-hydroxyanthranilic acid, and then to QUIN. 3-OH—KYN and QUIN act synergistically, i.e. 3-OH—KYN significantly potentiates the excitotoxic actions of QUIN. Studies from several laboratories have provided evidence that the shift of KYN pathway metabolism away from the 3-OH—KYN/QUIN branch to increase the formation of the neuroprotectant KYNA (kynurenic acid) in the brain leads to neuroprotection.

In addition to having effects in the brain, the inhibition of KMO is further contemplated to impact peripheral tissues. Based on the role of 3-OH-AA in the modulation of T(H)17 cells and IL-17/IL-23 balance in HIV pathogenesis, KMO inhibitors are predicted to prevent increase in microbial translocation across the gastrointestinal mucosa and systemic inflammation in long-term progressors. Thus, the inhibition of KMO may be useful in the treatment of peripheral HIV-related disorders as well as diseases of the brain.

Compounds and pharmaceutically acceptable salts thereof described herein that inhibit KMO are disclosed in PCT patent publications WO2013/033068 and WO2013/033085, each of which is incorporated herein by reference in its entirety.

There remains a need for methods and compositions that are effective in adjunctively treating disorders associated with HIV infection.

Accordingly, provided is a method of treating an HIV-related disorder in a subject infected with HIV, comprising adjunctively administering to a subject in need thereof a therapeutically effective amount of a compound of Formula I:

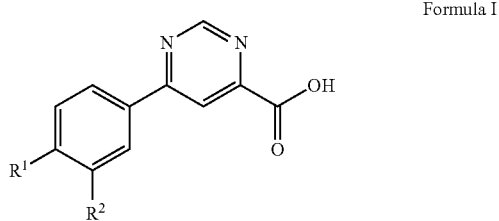

Formula I or a pharmaceutically acceptable salt thereof;
wherein the subject is also being administered an antiviral agent; and further wherein:

$R^1$ and $R^2$ are each independently selected from $C_1$-$C_4$ alkoxy optionally substituted with one $C_3$-$C_6$ cycloalkyl substituent, $C_1$-$C_4$ alkyl substituted with one substituent selected from $C_1$-$C_4$ alkoxy and $C_3$-$C_6$ cycloalkoxy, $C_3$-$C_6$ cycloalkoxy, and halo.

Also provided is a composition comprising an antiviral agent and a compound of Formula I:

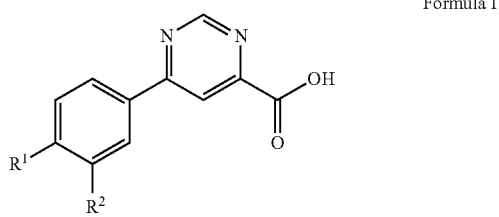

Formula I or a pharmaceutically acceptable salt thereof;
wherein:
$R^1$ and $R^2$ are each independently selected from $C_1$-$C_4$ alkoxy optionally substituted with one $C_3$-$C_6$ cycloalkyl substituent, $C_1$-$C_4$ alkyl substituted with one substituent selected from $C_1$-$C_4$ alkoxy and $C_3$-$C_6$ cycloalkoxy, $C_3$-$C_6$ cycloalkoxy, and halo.

Figure 1:
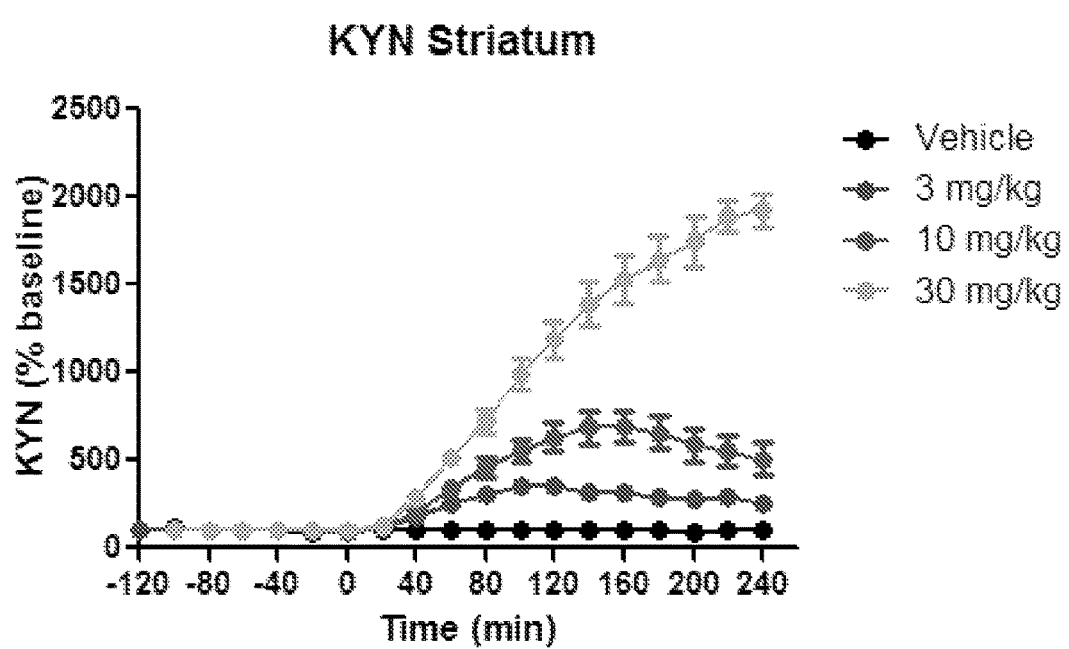
FIG. 1. shows the dose dependent increase of kynurenine (KYN) in the striatum extracellular space following dosing of Compound 6.

As used in the present specification, the following words, phrases and symbols are generally intended to have the meanings as set forth below, except to the extent that the context in which they are used indicates otherwise. The following abbreviations and terms have the indicated meanings throughout:

A dash ("—") that is not between two letters or symbols is used to indicate a point of attachment for a substituent. For example, —CONH$_2$ is attached through the carbon atom.

The term "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. By "cycloalkoxy" is meant a cycloalkyl group, as defined herein, that is likewise attached through an oxygen bridge.

The term "alkyl" encompasses straight chain and branched chain having the indicated number of carbon atoms, usually from 1 to 20 carbon atoms, for example 1 to 8 carbon atoms, such as 1 to 6 carbon atoms. For example C1-C6 alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and tert-butyl; "propyl" includes n-propyl and isopropyl.

The term "cycloalkyl" refers to a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

The term "halo" refers to fluoro, chloro, bromo, and iodo.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. The term "isomers" refers to different compounds that have the same molecular formula. The term "stereoisomers" refers to isomers that differ only in the way the atoms are arranged in space. The term "enantiomers" refers to stereoisomers that are non-superimposable mirror images of each other. A 1:1 mixture of a pair of enantiomers is a "racemic" mixture. The symbol "(±)" may be used to designate a racemic mixture where appropriate. The term "diastereoisomers" refers to stereoisomers that have at least two asymmetric atoms, but which are not mirror-images of each other. The term "meso compound" or "meso isomer" refers to a non-optically active member of a set of stereoisomers. Meso isomers contain two or more stereocenters but are not chiral (i.e., a plane of symmetry exists within the molecule). The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line.

Where compounds described herein exist in various tautomeric forms, the term "compound" includes all tautomeric forms of the compound. Such compounds also include crystal forms including polymorphs and clathrates. Similarly, the term "salt" includes all tautomeric forms and crystal forms of the compound. The term "tautomers" refers to structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Pharmaceutically acceptable forms of the compounds recited herein include pharmaceutically acceptable salts, prodrugs, and mixtures thereof. In some embodiments, the compounds described herein are in the form of pharmaceutically acceptable salts and prodrugs.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The term "prodrug" refers to a substance administered in an inactive or less active form that is then transformed (e.g., by metabolic processing of the prodrug in the body) into an active compound. The rationale behind administering a prodrug is to optimize absorption, distribution, metabolism, and/or excretion of the drug. Prodrugs may be obtained by making a derivative of an active compound (e.g., a compound of Formula I or another compound disclosed and/or described herein) that will undergo a transformation under the conditions of use (e.g., within the body) to form the active compound. The transformation of the prodrug to the active compound may proceed spontaneously (e.g., by way of a hydrolysis reaction) or it can be catalyzed or induced by another agent (e.g., an enzyme, light, acid or base, and/or temperature). The agent may be endogenous to the conditions of use (e.g., an enzyme present in the cells to which the prodrug is administered, or the acidic conditions of the stomach) or the agent may be supplied exogenously. Prodrugs can be obtained by converting one or more functional groups in the active compound into another functional group, which is then converted back to the original functional group when administered to the body. For example, a hydroxyl functional group can be converted to a sulfonate, phosphate, ester or carbonate group, which in turn can be hydrolyzed in vivo back to the hydroxyl group. Similarly, an amino functional group can be converted, for example, into an amide, carbamate, imine, urea, phosphenyl, phosphoryl or sulfenyl functional group, which can be hydrolyzed in vivo back to the amino group. A carboxyl functional group can be converted, for example, into an ester (including silyl esters and thioesters), amide or hydrazide functional group, which can be hydrolyzed in vivo back to the carboxyl group. Examples of prodrugs include, but are not limited to, phosphate, acetate, formate and benzoate derivatives of functional groups (such as alcohol or amine groups) present in the compounds of Formula I and other compounds disclosed and/or described herein. In some embodiments, the "prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives. Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

The compounds described herein can be enriched isotopic forms, e.g., enriched in the content of $^2H$, $^3H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, Curr. Pharm. Des., 2000; 6(10); Kabalka, G. et al., The Synthesis of Radiolabeled Compounds via Organometallic Intermediates, Tetrahedron, 1989, 45(21), 6601-21; and Evans, E., Synthesis of radiolabeled compounds, J. Radioanal. Chem., 1981, 64(1-2), 9-32.

A "solvate" refers to an entity formed by the interaction of a solvent and a compound or a pharmaceutically acceptable salt thereof. The term "compound" is intended to include solvates of compounds. Similarly, "salts" includes solvates of salts. Suitable solvates are pharmaceutically acceptable solvates, such as hydrates, including monohydrates and hemi-hydrates.

A "chelate" refers to an entity formed by the coordination of a compound to a metal ion at two (or more) points. The term "compound" is intended to include chelates of compounds. Similarly, "salts" includes chelates of salts.

A "non-covalent complex" refers to an entity formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen group containing a ring nitrogen or a heteroaryl group containing a ring nitrogen.

As used herein the terms "group", "radical" or "fragment" refer to a functional group or fragment of a molecule attachable to a bond or other fragments of molecules.

The term "active agent" refers to a compound or a pharmaceutically acceptable salt thereof which has biological activity. In some embodiments, an "active agent" is a compound or a pharmaceutically acceptable salt thereof having pharmaceutical utility. For example an active agent may be an anti-neurodegenerative therapeutic or an antiviral therapeutic.

The term "therapeutically effective amount" of a compound, or a pharmaceutically acceptable salt thereof, described herein, refers to an amount effective, when administered to a human or non-human subject, to provide a therapeutic benefit such as amelioration of symptoms, slowing of disease progression, or prevention of disease e.g., a therapeutically effective amount may be an amount sufficient to decrease the symptoms of a disease responsive to inhibition of KMO activity and modulation of kynurenine pathway metabolites (such as kynurenine, kynurenic acid, anthranilic acid, 3-OH-kynurenine, 3-OH anthranilic acid, or quinolinic acid). In some embodiments, a therapeutically effective amount is an amount sufficient to treat the symptoms of an HIV-related disorder. In some embodiments a therapeutically effective amount is an amount sufficient to reduce the signs or side effects of an HIV-related disorder. In some embodiments, a therapeutically effective amount of a compound or a pharmaceutically acceptable salt thereof is an amount sufficient to prevent a significant increase or significantly reduce the level of HIV-related neuronal cell death. In some embodiments, a therapeutically effective amount of a compound or a pharmaceutically acceptable salt thereof is an amount sufficient to prevent a significant increase or significantly reduce the level of QUIN associated with HIV-related neuronal cell death. In some embodiments, a therapeutically effective amount is an amount sufficient to effect an increase in the level of KYNA associated with neuronal cell health in an HIV-infected patient. In some embodiments, a therapeutically effective amount is an amount sufficient to increase the anticonvulsant and neuroprotective properties associated with lowered levels of QUIN and increased levels of KYNA in an HIV-infected patient. In some embodiments, a therapeutically effective amount is an amount sufficient to modulate an inflammatory process in an HIV-infected patient, including but not limited to inflammation in the brain, spinal cord, and peripheral nervous system, or meninges. In methods described herein for adjunctively treating an HIV-related disorder, a therapeutically effective amount may also be an amount sufficient, when administered to a patient, to detectably slow the progression of the HIV-related disorder, or prevent the patient to whom the composition is given from presenting symptoms of the HIV-related disorder. In some methods described herein for treating an HIV-related disorder, a therapeutically effective amount may also be an amount sufficient to produce a detectable decrease in the level of HIV-related neuronal cell death. For example, in some embodiments a therapeutically effective amount is an amount sufficient to significantly decrease the level of HIV-related neuronal death by effecting a detectable decrease in the amount of QUIN, and an increase in the amount of kynurenine, KYNA, or anthranilic acid. In addition, an amount is considered to be a therapeutically effective amount if it is characterized as such by at least one of the above criteria or experimental conditions, regardless of any inconsistent or contradictory results under a different set of criteria or experimental conditions.

The term "inhibition" indicates a significant decrease in the baseline activity of a biological activity or process. "Inhibition of KMO activity" refers to a decrease in KMO activity as a direct or indirect response to the presence of at least one compound or a pharmaceutically acceptable salt thereof described herein, relative to the activity of KMO in the absence of at least one compound or a pharmaceutically acceptable salt thereof. The decrease in activity may be due to the direct interaction of the compound or a pharmaceutically acceptable salt thereof with KMO, or due to the interaction of the compound or a pharmaceutically acceptable salt thereof described herein with one or more other factors that in turn affect KMO activity. For example, the presence of the compound or a pharmaceutically acceptable salt thereof may decrease KMO activity by directly binding to the KMO, by causing (directly or indirectly) another factor to decrease KMO activity, or by (directly or indirectly) decreasing the amount of KMO present in the cell or organism. Inhibition of KMO activity also refers to an observable inhibition of 3-HK and QUIN production in a standard assay such as the assays described below. The inhibition of KMO activity also refers to an observable increase in the production of KYNA. In some embodiments, the compound or a pharmaceutically acceptable salt thereof described herein has an $IC_{50}$ value less than or equal to 1 micromolar. In some embodiments, the compound or a pharmaceutically acceptable salt thereof has an $IC_{50}$ value less than or equal to less than 100 micromolar. In some embodiments, the compound or a pharmaceutically acceptable salt thereof has an $IC_{50}$ value less than or equal to 10 nanomolar. Inhibition of KMO activity also refers to activation, redistribution, reorganization, or capping of one or more various KMO membrane-associated proteins (such as those receptors found in the mitochondria), or binding sites can undergo redistribution and capping that can initiate signal transduction. KMO activity also can modulate the availability of kynurenine, which can effect the synthesis or production of QUIN, KYNA, anthranilic acid, and/or 3-HK.

A "disease responsive to inhibition of KMO activity" refers to a disease in which inhibiting KMO provides a therapeutic benefit such as an amelioration of symptoms, decrease in disease progression, prevention or delay of disease onset, prevention or amelioration of an inflammatory response, or inhibition of aberrant activity and/or death of certain cell-types (such as neuronal cells).

"Treatment" or "treating" refers to any treatment of a disease in a patient, including: a) preventing the disease, that is, causing the clinical symptoms of the disease not to develop; b) inhibiting the progression of the disease; c) slowing or arresting the development of clinical symptoms; and/or d) relieving the disease, that is, causing the regression of clinical symptoms.

"Subject" or "patient' refers to an animal, such as a mammal, that has been or will be the object of treatment, observation or experiment. The methods described herein may be useful in both human therapy and veterinary applications. In some embodiments, the subject is a mammal; and in some embodiments the subject is human.

The term "disease" refers to an abnormal condition of the human or animal body or of one or more of its parts that impairs normal functioning, is typically manifested by distinguishing signs and symptoms, and causes the human or animal to have a reduced duration or quality of life. As used herein is intended to be generally synonymous, and is used interchangeably with, the terms "disorder" and "condition" (as in medical condition).

The term "adjunctively" refers to the administering to a patient, or treating a patient with, at least one compound, or a pharmaceutically acceptable salt thereof, described herein, in addition to an antiviral agent, either simultaneously, or at intervals prior to, during, or following administration of the antiviral agent to achieve the desired therapeutic effect.

The term "viral load" refers to the concentration of a virus, such as HIV, in the blood.

Provided is a composition comprising an antiviral agent and a compound of Formula I:

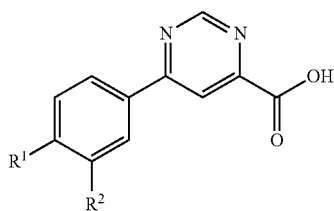

Formula I or a pharmaceutically acceptable salt thereof;
wherein:
$R^1$ and $R^2$ are each independently selected from $C_1$-$C_4$ alkoxy optionally substituted with one $C_3$-$C_6$ cycloalkyl substituent, $C_1$-$C_4$ alkyl substituted with one substituent selected from $C_1$-$C_4$ alkoxy and $C_3$-$C_6$ cycloalkoxy, $C_3$-$C_6$ cycloalkoxy, and halo.

In some embodiments, $R^1$ is $C_1$-$C_4$ alkoxy optionally substituted with one $C_3$-$C_6$ cycloalkyl substituent.

In some embodiments, $R^1$ is $C_1$-$C_4$ alkoxy.

In some embodiments, $R^1$ is sec-butoxy.

In some embodiments, $R^1$ is (R)-sec-butoxy.

In some embodiments, $R^1$ is (S)-sec-butoxy.

In some embodiments, $R^1$ is isopropoxy.

In some embodiments, $R^1$ is $C_1$-$C_4$ alkoxy substituted with one $C_3$-$C_6$ cycloalkyl substituent.

In some embodiments, $R^1$ is cyclopropylmethoxy.

In some embodiments, $R^1$ is $C_1$-$C_4$ alkyl substituted with one substituent selected from $C_1$-$C_4$ alkoxy and $C_3$-$C_6$ cycloalkoxy.

In some embodiments, $R^1$ is $C_1$-$C_4$ alkyl substituted with one $C_1$-$C_4$ alkoxy substituent.

In some embodiments, $R^1$ is 1-methoxyethyl.

In some embodiments, $R^1$ is methoxymethyl.

In some embodiments, $R^1$ is $C_1$-$C_4$ alkyl substituted with one $C_3$-$C_6$ cycloalkoxy substituent.

In some embodiments, $R^1$ is 1-cyclopropoxyethyl.

In some embodiments, $R^1$ is cyclopropoxymethyl.

In some embodiments, $R^1$ is $C_3$-$C_6$ cycloalkoxy.

In some embodiments, $R^1$ is cyclobutoxy.

In some embodiments, $R^1$ is cyclopentyloxy.

In some embodiments, $R^1$ is cyclopropoxy.

In some embodiments, $R^1$ is halo.

In some embodiments, $R^1$ is chloro.

In some embodiments, $R^1$ is fluoro.

In some embodiments, $R^2$ is selected from: $C_1$-$C_4$ alkoxy, $C_3$-$C_6$ cycloalkoxy, and halo.

In some embodiments, $R^2$ is $C_1$-$C_4$ alkoxy.

In some embodiments, $R^2$ is isobutoxy.

In some embodiments, $R^2$ is isopropoxy.

In some embodiments, $R^2$ is methoxy.

In some embodiments, $R^2$ is $C_3$-$C_6$ cycloalkoxy.

In some embodiments, $R^2$ is cyclopropoxy.

In some embodiments, $R^2$ is halo.

In some embodiments, $R^2$ is chloro.

In some embodiments, $R^2$ is fluoro.

In some embodiments, $R^1$ is selected from $C_1$-$C_4$ alkoxy optionally substituted with one $C_3$-$C_6$ cycloalkyl substituent, $C_1$-$C_4$ alkyl substituted with one substituent selected from $C_1$-$C_4$ alkoxy and $C_3$-$C_6$ cycloalkoxy, $C_3$-$C_6$ cycloalkoxy, and halo; and $R^2$ is selected from: $C_1$-$C_4$ alkoxy, $C_3$-$C_6$ cycloalkoxy, and halo.

In some embodiments, $R^1$ is selected from sec-butoxy, chloro, cyclobutoxy, cyclopentyloxy, cyclopropoxy, 1-cyclopropoxyethyl, cyclopropylmethoxy, cyclopropoxymethyl, fluoro, methoxy, 1-methoxyethyl, and methoxymethyl; and $R^2$ is selected from: chloro, cyclopropoxy, fluoro, isobutoxy, isopropoxy, and methoxy.

In some embodiments, the compound of Formula I is selected from:
6-(4-chloro-3-methoxyphenyl)pyrimidine-4-carboxylic acid;
6-(3-chloro-4-isopropoxyphenyl)pyrimidine-4-carboxylic acid;
6-(3-chloro-4-(cyclopentyloxy)phenyl)pyrimidine-4-carboxylic acid;
(S)-6-(4-sec-butoxy-3-chlorophenyl)pyrimidine-4-carboxylic acid;
(R)-6-(4-sec-butoxy-3-chlorophenyl)pyrimidine-4-carboxylic acid;
6-(3-chloro-4-cyclopropoxyphenyl)pyrimidine-4-carboxylic acid;
6-(3-chloro-4-cyclobutoxyphenyl)pyrimidine-4-carboxylic acid;
6-(3-chloro-4-(cyclopropylmethoxy)phenyl)pyrimidine-4-carboxylic acid;
6-(3-chloro-4-(methoxymethyl)phenyl)pyrimidine-4-carboxylic acid;
6-(3-chloro-4-(1-methoxyethyl)phenyl)pyrimidine-4-carboxylic acid;
6-(3-chloro-4-(cyclopropoxymethyl)phenyl)pyrimidine-4-carboxylic acid;
6-(3-chloro-4-(1-cyclopropoxyethyl)phenyl)pyrimidine-4-carboxylic acid;
6-(4-chloro-3-cyclopropoxyphenyl)pyrimidine-4-carboxylic acid;
6-(4-chloro-3-isopropoxyphenyl)pyrimidine-4-carboxylic acid;
6-(4-chloro-3-fluorophenyl)pyrimidine-4-carboxylic acid;
6-(3-chloro-4-fluorophenyl)pyrimidine-4-carboxylic acid;
6-(3,4-dichlorophenyl)pyrimidine-4-carboxylic acid;
6-(3,4-difluorophenyl)pyrimidine-4-carboxylic acid; and
6-(3-chloro-4-methoxy)pyrimidine-4-carboxylic acid.

In some embodiments, the compound of Formula I is 6-(4-chloro-3-methoxyphenyl)pyrimidine-4-carboxylic acid.

In some embodiments, the compound of Formula I is 6-(3-chloro-4-isopropoxyphenyl)pyrimidine-4-carboxylic acid.

In some embodiments, the compound of Formula I is 6-(3-chloro-4-(cyclopentyloxy)phenyl)pyrimidine-4-carboxylic acid.

In some embodiments, the compound of Formula I is (S)-6-(4-sec-butoxy-3-chlorophenyl)pyrimidine-4-carboxylic acid.

In some embodiments, the compound of Formula I is (R)-6-(4-sec-butoxy-3-chlorophenyl)pyrimidine-4-carboxylic acid.

In some embodiments, the compound of Formula I is 6-(3-chloro-4-cyclopropoxyphenyl)pyrimidine-4-carboxylic acid.

In some embodiments, the compound of Formula I is 6-(3-chloro-4-cyclobutoxyphenyl)pyrimidine-4-carboxylic acid.

In some embodiments, the compound of Formula I is 6-(3-chloro-4-(cyclopropylmethoxy)phenyl)pyrimidine-4-carboxylic acid.

In some embodiments, the compound of Formula I is 6-(3-chloro-4-(methoxymethyl)phenyl)pyrimidine-4-carboxylic acid.

In some embodiments, the compound of Formula I is 6-(3-chloro-4-(1-methoxyethyl)phenyl)pyrimidine-4-carboxylic acid.

In some embodiments, the compound of Formula I is 6-(3-chloro-4-(cyclopropoxymethyl)phenyl)pyrimidine-4-carboxylic acid.

In some embodiments, the compound of Formula I is 6-(3-chloro-4-(1-cyclopropoxyethyl)phenyl)pyrimidine-4-carboxylic acid.

In some embodiments, the compound of Formula I is 6-(4-chloro-3-cyclopropoxyphenyl)pyrimidine-4-carboxylic acid.

In some embodiments, the compound of Formula I is 6-(4-chloro-3-isopropoxyphenyl)pyrimidine-4-carboxylic acid.

In some embodiments, the compound of Formula I is 6-(4-chloro-3-fluorophenyl)pyrimidine-4-carboxylic acid.

In some embodiments, the compound of Formula I is 6-(3-chloro-4-fluorophenyl)pyrimidine-4-carboxylic acid.

In some embodiments, the compound of Formula I is 6-(3,4-dichlorophenyl)pyrimidine-4-carboxylic acid.

In some embodiments, the compound of Formula I is 6-(3,4-difluorophenyl)pyrimidine-4-carboxylic acid.

In some embodiments, the compound of Formula I is 6-(3-chloro-4-methoxy)pyrimidine-4-carboxylic acid.

Also provided is a composition comprising an antiviral agent and a compound selected from the compounds shown in Table A below, or a pharmaceutically acceptable salt thereof.

TABLE A

| Compound No. | Chemical Structure | Chemical Name |
|---|---|---|
| 1 | 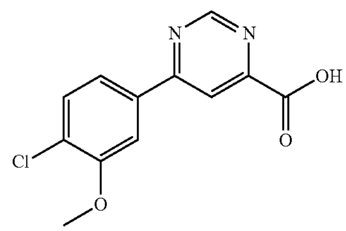 [SMILES: COc1cc(-c2cc(C(=O)O)ncn2)ccc1Cl] | 6-(4-chloro-3-methoxy-phenyl)pyrimidine-4-carboxylic acid |
| 2 | 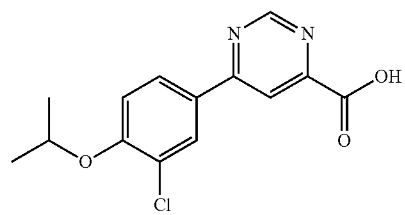 [SMILES: CC(C)Oc1ccc(-c2cc(C(=O)O)ncn2)cc1Cl] | 6-(3-chloro-4-isopropoxy-phenyl)pyrimidine-4-carboxylic acid |
| 3 | 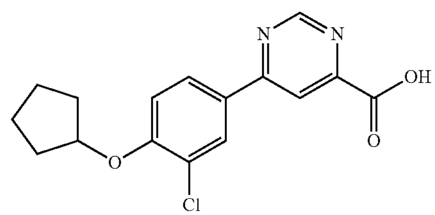 [SMILES: O=C(O)c1cc(-c2ccc(OC3CCCC3)c(Cl)c2)ncn1] | 6-(3-chloro-4-(cyclopentyloxy)-phenyl)pyrimidine-4-carboxylic acid |
| 4 | 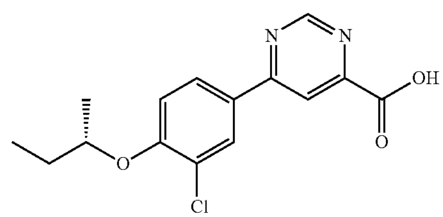 [SMILES: CC[C@H](C)Oc1ccc(-c2cc(C(=O)O)ncn2)cc1Cl] | (S)-6-(4-sec-butoxy-3-chloro-phenyl)pyrimidine-4-carboxylic acid |
| 5 | 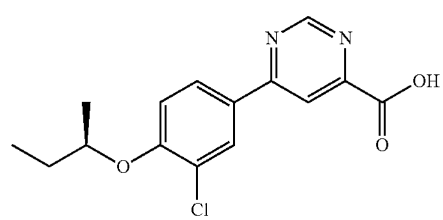 [SMILES: CC[C@@H](C)Oc1ccc(-c2cc(C(=O)O)ncn2)cc1Cl] | (R)-6-(4-sec-butoxy-3-chloro-phenyl)pyrimidine-4-carboxylic acid |
| 6 | 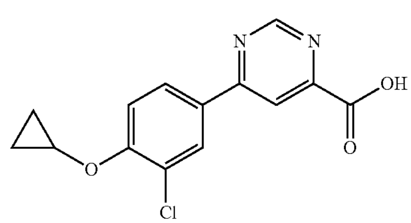 [SMILES: O=C(O)c1cc(-c2ccc(OC3CC3)c(Cl)c2)ncn1] | 6-(3-chloro-4-cyclopropoxy-phenyl)pyrimidine-4-carboxylic acid |

TABLE A-continued

| Compound No. | Chemical Structure | Chemical Name |
|---|---|---|
| 7 | 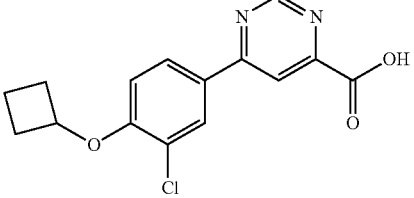 | 6-(3-chloro-4-cyclobutoxy-phenyl)pyrimidine-4-carboxylic acid |
| 8 | 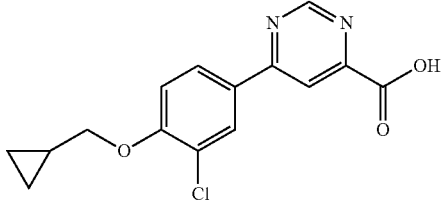 [SMILES: O=C(O)c1cc(-c2ccc(OCC3CC3)c(Cl)c2)ncn1] | 6-(3-chloro-4-(cyclopropylmethoxy)-phenyl)pyrimidine-4-carboxylic acid |
| 9 | 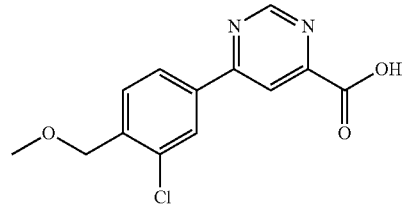 [SMILES: COCc1ccc(-c2cc(C(=O)O)ncn2)cc1Cl] | 6-(3-chloro-4-(methoxymethyl)-phenyl)pyrimidine-4-carboxylic acid |
| 10 | 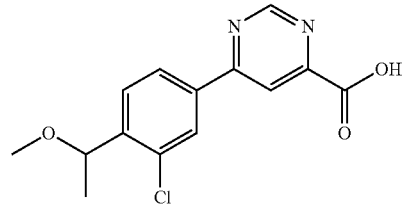 [SMILES: COC(C)c1ccc(-c2cc(C(=O)O)ncn2)cc1Cl] | 6-(3-chloro-4-(1-methoxyethyl)-phenyl)pyrimidine-4-carboxylic acid |
| 11 | 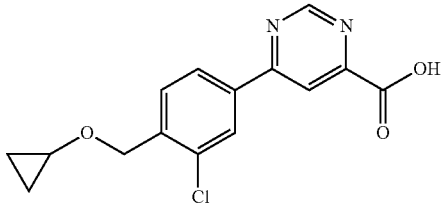 [SMILES: O=C(O)c1cc(-c2ccc(COC3CC3)c(Cl)c2)ncn1] | 6-(3-chloro-4-(cyclopropoxymethyl)-phenyl)pyrimidine-4-carboxylic acid |
| 12 | 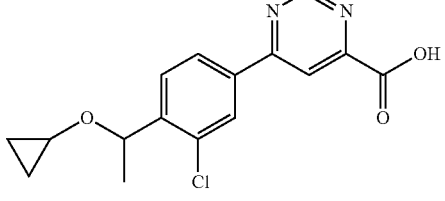 | 6-(3-chloro-4-(1-cyclopropoxyethyl)-phenyl)pyrimidine-4-carboxylic acid |
| 13 | 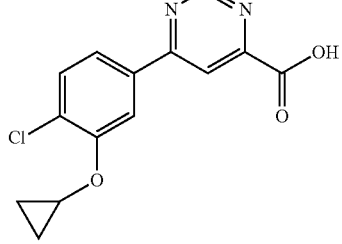 | 6-(4-chloro-3-cyclopropoxy-phenyl)pyrimidine-4-carboxylic acid |

TABLE A-continued

| Compound No. | Chemical Structure | Chemical Name |
|---|---|---|
| 14 | 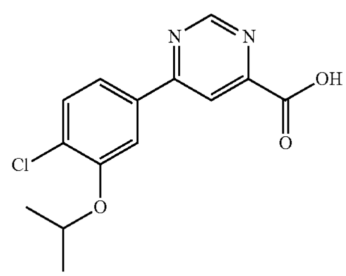 [SMILES: CC(C)Oc1cc(-c2cc(C(=O)O)ncn2)ccc1Cl] | 6-(4-chloro-3-isopropoxy-phenyl)pyrimidine-4-carboxylic acid |
| 15 | 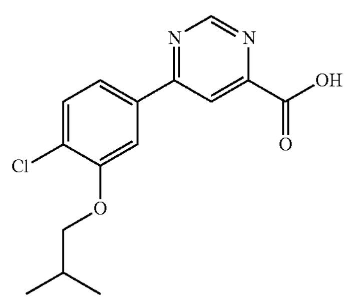 [SMILES: CC(C)COc1cc(-c2cc(C(=O)O)ncn2)ccc1Cl] | 6-(4-chloro-3-isobutoxy-phenyl)pyrimidine-4-carboxylic acid |
| 16 | 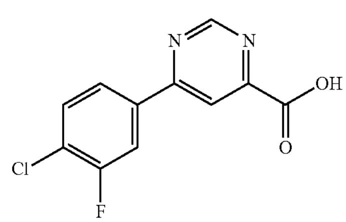 [SMILES: O=C(O)c1cc(-c2ccc(Cl)c(F)c2)ncn1] | 6-(4-chloro-3-fluoro-phenyl)pyrimidine-4-carboxylic acid |
| 17 | 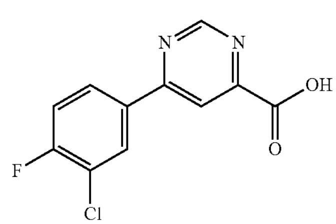 [SMILES: O=C(O)c1cc(-c2ccc(F)c(Cl)c2)ncn1] | 6-(3-chloro-4-fluoro-phenyl)pyrimidine-4-carboxylic acid |
| 18 | 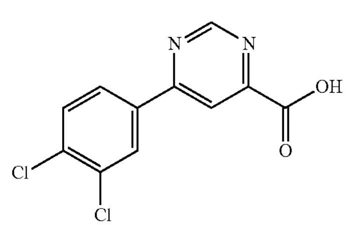 [SMILES: O=C(O)c1cc(-c2ccc(Cl)c(Cl)c2)ncn1] | 6-(3,4-dichloro-phenyl)pyrimidine-4-carboxylic acid |
| 19 | 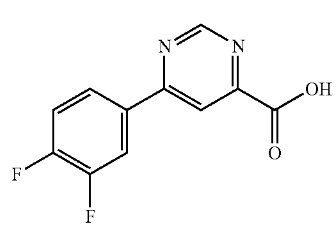 [SMILES: O=C(O)c1cc(-c2ccc(F)c(F)c2)ncn1] | 6-(3,4-difluoro-phenyl)pyrimidine-4-carboxylic acid |

TABLE A-continued

| Compound No. | Chemical Structure | Chemical Name |
|---|---|---|
| 20 | 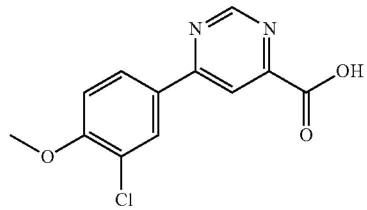 [SMILES: COc1ccc(-c2cc(C(=O)O)ncn2)cc1Cl] | 6-(3-chloro-4-methoxy)pyrimidine-4-carboxylic acid |

Methods for obtaining the compounds, or pharmaceutically acceptable salts thereof, described herein will be apparent to those of ordinary skill in the art, suitable procedures being described, for example, in examples below, and in the references cited herein.

Provided is a method of treating a disorder in a subject infected with HIV, comprising adjunctively administering to a subject in need thereof a therapeutically effective amount of a compound of Formula I:

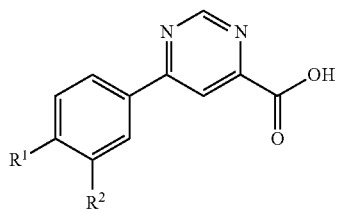

Formula I or a pharmaceutically acceptable salt thereof;
wherein the subject is also being administered an antiviral agent; and
further wherein:
$R^1$ and $R^2$ are each independently selected from $C_1$-$C_4$ alkoxy optionally substituted with one $C_3$-$C_6$ cycloalkyl substituent, $C_1$-$C_4$ alkyl substituted with one substituent selected from $C_1$-$C_4$ alkoxy and $C_3$-$C_6$ cycloalkoxy, $C_3$-$C_6$ cycloalkoxy, and halo.

Provided is a method of lowering HIV viral load in a subject infected with HIV, comprising adjunctively administering to a subject in need thereof a therapeutically effective amount of a compound of Formula I:

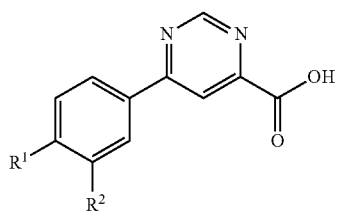

Formula I or a pharmaceutically acceptable salt thereof;
wherein the subject is also being administered an antiviral agent; and
further wherein:
$R^1$ and $R^2$ are each independently selected from $C_1$-$C_4$ alkoxy optionally substituted with one $C_3$-$C_6$ cycloalkyl substituent, $C_1$-$C_4$ alkyl substituted with one substituent selected from $C_1$-$C_4$ alkoxy and $C_3$-$C_6$ cycloalkoxy, $C_3$-$C_6$ cycloalkoxy, and halo.

HIV drugs are classified into six drug classes on the basis of how each drug interferes with the HIV life cycle. These six classes include the nucleoside/nucleotide reverse transcriptase inhibitors (NRTIs), non-nucleoside reverse transcriptase inhibitors (NNRTIs), protease inhibitors (PIs), fusion inhibitors, CCR5 antagonists, and integrase strand transfer inhibitors (INSTIs). HIV uses reverse transcriptase (RT) to convert its RNA into DNA (reverse transcription). Blocking RT and reverse transcription prevents HIV from replicating. NRTIs lack a 3' hydroxyl group and are metabolically activated by host cellular kinases to their corresponding 5'-triphosphate forms, which are subsequently incorporated into DNA by HIV reverse transcriptase (RT) and which act as chain terminators of DNA synthesis. Examples of NRTIs include amdoxovir, Combivir® (lamivudine/zidovudine), Emtriva® (emtricitabine), Epivir® (lamivudine), Epzicom® (abacavir/lamivudine), Retrovir® (zidovudine), tenofovir alafenamide fumarate, Trizivir® (abacavir/lamivudine/zidovudine), Truvada® (emtricitabine/tenofovir), Videx® (didanosine), Videx® EC (didanosine), Viread® (tenofovir disoproxil), Zerit® (stavudine), and Ziagen® (abacavir). NNRTIs are noncompetitive inhibitors of DNA polymerization, binding to a hydrophobic pocket in RT near the polymerase active site. Examples of NRTIs include Edurant® (rilpivirine), Intelence® (etravirine), lersivirine, Rescriptor® (delavirdine), Sustiva® (efavirenz), Viramune® (nevirapine), and Viramune® XR (nevirapine). After transcription in the nucleus, viral mRNA enters the cytoplasm and uses the host's cellular machinery to manufacture virus proteins. The viral components then gather at the cell membrane and immature viruses bud off the cell. Core proteins are produced as part of long polypeptides, which must be cut into smaller fragments by the enzyme protease in order to form mature, functional proteins. PIs bind to the site where protein cutting occurs, and so prevent the enzyme from releasing the individual core proteins. In this way the new viral particles are unable to mature or become infectious. Examples of PIs include Aptivus® (tipranavir), Crixivan® (indinavir sulfate), Invirase® (saquinavir mesylate), Kaletra® (lopinavir/ritonavir), Lexiva® (fosamprenavir), Norvir® (ritonavir), Prezista® (darunavir), Reyataz® (atazanavir), and Viracept® (nelfinavir). Fusion inhibitors block the HIV envelope from merging with the host cell membrane (fusion), which prevents HIV from entering the host cell. Examples of fusion inhibitors include Fuzeon® (enfuvirtide). CCR5 antagonists block the CCR5 receptor on the surface of certain immune cells, such as CD4+ cells, which prevents HIV from entering the cell. Examples of CCR5 antagonists include cenicriviroc and Selzentry® (maraviroc). INSTIs block integrase, an enzyme HIV uses to insert (integrate) its viral DNA into the DNA of the host cell. Blocking integrase prevents HIV from replicating. Examples of INSTIs include Isentress® (raltegravir), Tivicay® (dolutegravir), and Elvitegravir. Multi-class combination drugs include Atripla® (efavirenz+tenofovir+emtricitabine), Complera® (rilpivirine+tenofovir+emtricitabine), Stribild® (elvitegravir+cobicistat+tenofovir+emtricitabine), and Trii™ (dolutegravir+abacavir+lamivudine). Recommended antiretroviral therapy (ART) regimens for the treatment of HIV involve using a combination of three or more antiretroviral (ARV) drugs from at least two different HIV drug classes. The current standard of care for HIV/AIDS in the developed world is highly active antiretroviral therapy (HAART) therapy, usually a combination of two reverse transcriptase inhibitors and a protease inhibitor. Class-sparing regimens purposefully exclude all ARV drugs from a specific drug class to save specific ARV drugs for future use in case a regimen needs to be changed because of toxicity or drug resistance. A class-sparing regimen may also be used to avoid adverse effects associated with a specific drug class. Certain HIV ART regimens include a pharmacokinetic enhancer that increases the level of certain ARVs in the blood and make them more effective. Examples of pharmacokinetic enhancers include Cobicistat, a component of the approved fixed-dose combination tablet Stribild®; ritonavir, a PI that improves the pharmacokinetic (PK) profiles of concomitant PIs; and SPI-452. Experimental immune-based HIV therapies include, Aralen® (chloroquine), DermaVir, interleukin-7, lexgenleucel-T, Plaquenil® (hydroxychloroquine), Proleukin® (aldesleukin), and SB-728-T. Entry inhibitors are a class of ARVs that include fusion inhibitors, CCR5 antagonists, and glycosidase inhibitors. Maturation inhibitors are a class of ARVs that target the gag polyprotein precursor, the main structural protein responsible for assembly and budding of virion particles during maturation.

In some embodiments, the antiviral agent is selected from: entry inhibitors, fusion inhibitors, glycosidase inhibitors, CCR5 antagonists, immune-based therapies, integrase inhibitors, maturation inhibitors, multi-class combination drugs, non-nucleoside reverse transcriptase inhibitors, nucleoside/nucleotide reverse transcriptase inhibitors, pharmacokinetic enhancers, and protease inhibitors, and combinations thereof.

In some embodiments, the antiviral agent is selected from: nucleoside/nucleotide reverse transcriptase inhibitors, non-nucleoside reverse transcriptase inhibitors, protease inhibitors, fusion inhibitors, CCR5 antagonists, and integrase strand transfer inhibitors, and combinations thereof.

In some embodiments, the antiviral agent is selected from: amdoxovir, Aptivus® (tipranavir), Aralen® (chloroquine), Atripla® (efavirenz/emtricitabine/tenofovir), cenicriviroc, Cobicistat, Combivir® (lamivudine/zidovudine), Complera® (emtricitabine/rilpivirine/tenofovir), Crixivan® (indinavir sulfate), DermaVir, Edurant® (rilpivirine), elvitegravir, Emtriva® (emtricitabine), Epivir® (lamivudine), Epzicom® (abacavir/lamivudine), Fuzeon® (enfuvirtide), ibalizumab, Intelence® (etravirine), interleukin-7, Invirase® (saquinavir mesylate), Isentress® (raltegravir), Kaletra® (lopinavir/ritonavir), lersivirine, lexgenleucel-T, Lexiva® (fosamprenavir), Norvir® (ritonavir), Plaquenil® (hydroxychloroquine), Proleukin® (aldesleukin), Prezista® (darunavir), PRO 140, Rescriptor® (delavirdine), Retrovir® (zidovudine), Reyataz® (atazanavir), SB-728-T, Selzentry® (maraviroc), SPI-452, Stribild® (elvitegravir/cobicistat/emtricitabine/tenofovir), Sustiva® (efavirenz), tenofovir alafenamide fumarate, Tivicay® (dolutegravir), Trii™ (dolutegravir/abacavir/lamivudine), Trizivir® (abacavir/lamivudine/zidovudine), Truvada® (emtricitabine/tenofovir), Videx® (didanosine), Videx® EC (didanosine), Viracept® (nelfinavir), Viramune® (nevirapine), Viramune® XR (nevirapine), Viread® (tenofovir disoproxil), Zerit® (stavudine), and Ziagen® (abacavir), and combinations thereof.

In some embodiments, the antiviral agent is HAART.

Human Immunodeficiency Virus (HIV) is the virus that causes Acquired Immunodeficiency Syndrome (AIDS), which is the most advanced stage of HIV infection. HIV destroys the CD4(+) T lymphocytes (CD4(+) cells) of the immune system, leaving the body vulnerable to life-threatening infections and cancers. HIV is a retrovirus that occurs as two types: HIV-1 and HIV-2. Both types are transmitted through direct contact with HIV-infected body fluids, such as blood, semen, and genital secretions, or from an HIV-infected mother to her child during pregnancy, birth, or breastfeeding (through breast milk). HIV-1 can be classified into four groups: M Group, N Group, O Group, and P Group. Viruses within each group can then be further classified by subtype. For example, the HIV-1 M group includes at least nine subtypes: A1, A2, B, C, D, F1, F2, G, H, J, and K. HIV-2 infection is endemic to West Africa. It generally takes longer to progress to symptomatic HIV/AIDS and has a lower mortality rate than HIV-1 infection.

In some embodiments, the HIV is HIV-1.

In some embodiments, the HIV is HIV-1 M group.

In some embodiments, the HIV is HIV-1 M group subtype A1.

In some embodiments, the HIV is HIV-1 M group subtype A2.

In some embodiments, the HIV is HIV-1 M group subtype B.

In some embodiments, the HIV is HIV-1 M group subtype C.

In some embodiments, the HIV is HIV-1 M group subtype D.

In some embodiments, the HIV is HIV-1 M group subtype F1.

In some embodiments, the HIV is HIV-1 M group subtype F2.

In some embodiments, the HIV is HIV-1 M group subtype G.

In some embodiments, the HIV is HIV-1 M group subtype H.

In some embodiments, the HIV is HIV-1 M group subtype J.

In some embodiments, the HIV is HIV-1 M group subtype K.

In some embodiments, the HIV is HIV-1 N Group.

In some embodiments, the HIV is HIV-1 O Group.

In some embodiments, the HIV is HIV-1 P Group.

In some embodiments, the HIV is HIV-2.

HIV enters the central nervous system (CNS) early in the course of the infection and causes several important CNS conditions over the course of the disease, such as HIV encephalopathy and AIDS dementia complex. As part of the acute HIV syndrome during seroconversion, patients may experience HIV encephalopathy. HIV-associated progressive encephalopathy (HPE) is a syndrome complex with cognitive, motor, and behavioral features seen in children. Prior to the advent of highly active antiretroviral therapy (HAART), dementia was a common source of morbidity and mortality in HIV-infected patients. It was usually observed in the late stages of AIDS, when CD4(+) lymphocyte counts fall below 200 cells/mL, and was seen in up to 50% of patients prior to their deaths. In 1986, the term AIDS dementia complex (ADC) was introduced to describe a unique constellation of neurobehavioral findings. HIV associated neurocognitive disorder (HAND) encompasses a hierarchy of progressively more severe patterns of neurological involvement. It can range from asymptomatic neurocognitive impairment (ANI) to minor neurocognitive disorder (MND) to more severe HIV-associated dementia (HAD) (also called AIDS dementia complex [ADC] or HIV encephalopathy). ADC is considered a single entity with a broad and varied spectrum of clinical manifestations and severity. ADC is characterized by cognitive, motor, and behavioral features in adults, usually those with advanced AIDS. With the advent of HAART, a less severe dysfunction, minor cognitive motor disorder (MCMD), has become more common than ADC. The overall psychosocial and emotional burden on the family and friends of patients with HIV dementia is tremendous, far beyond that of a cognitively intact patient with AIDS. Patients with cognitive difficulties have problems with compliance and adherence to their medication regimen. Because of their neuropsychiatric problems, these patients are likely to be less inhibited and are more prone to HIV-related risk behavior (e.g., unprotected intercourse), and they therefore pose a greater risk of transmission of the virus. In addition to HIV itself, other causes of neurologic complications in HIV-infected individuals include opportunistic infections, tumors, and anti-retroviral drugs. Other neurologic complications that arise from primary HIV infection include vacuolar myelopathy, peripheral neuropathies, and polymyositis.

In some embodiments, the HIV-related disorder is an opportunistic infection selected from: *candidiasis, coccidioidomycosis, cryptococcosis, cryptosporidiosis, cytomegalovirus*, herpes simplex virus, herpes zoster, *histoplasmosis, isosporiasis, mycobacterium avium* complex, *pneumocystis pneumonia*, bacterial pneumonia, progressive multifocal *leukoencephalopathy salmonella, toxoplasmosis*, and *tuberculosis*.

In some embodiments, the HIV-related disorder is an AIDS-related cancer selected from: cervical cancer, Kaposi sarcoma, and lymphomas.

In some embodiments, the HIV-related disorder is an AIDS-defining illnesses selected from: *candidiasis* of the esophagus, bronchi, trachea, or lungs, invasive cervical cancer, disseminated or extrapulmonary *coccidioidomycosis*, extrapulmonary *cryptococcosis*, chronic intestinal *cryptosporidiosis, cytomegalovirus* disease (other than liver, spleen, or nodes), *cytomegalovirus retinitis* with loss of vision, HIV related-encephalopathy, herpes simplex (with chronic ulcers, bronchitis, pneumonitis, or esophagitis), disseminated or extrapulmonary histoplasmosis, chronic intestinal isosporiasis, Kaposi sarcoma, Burkitt's lymphoma, immunoblastic lymphoma, primary lymphoma of brain, disseminated or extrapulmonary *mycobacterium avium* complex or *M. kansasii*, pulmonary or extrapulmonary *mycobacterium tuberculosis*, disseminated or extrapulmonary *mycobacterium* species, *pneumocystis jiroveci* pneumonia, recurrent pneumonia, progressive multifocal *leukoencephalopathy*, recurrent *salmonella septicemia*, toxoplasmosis of brain, and wasting syndrome due to HIV.

In some embodiments, the HIV-related disorder is a neurological disorder.

In some embodiments, the neurological disorder is selected from: AIDS dementia complex, AIDS-induced encephalopathy, HIV encephalopathy, HIV-associated progressive encephalopathy, HIV-associated neurocognitive disorder, asymptomatic neurocognitive impairment, minor neurocognitive disorder, HIV-associated dementia, minor cognitive motor disorder, vacuolar myelopathy, peripheral neuropathies, and polymyositis.

In some embodiments, the neurological disorder is AIDS dementia complex.

In some embodiments, the neurological disorder is AIDS-induced encephalopathy.

In some embodiments, the neurological disorder is HIV encephalopathy.

In some embodiments, the neurological disorder is HIV-associated progressive encephalopathy.

In some embodiments, the neurological disorder is HIV-associated neurocognitive disorder.

In some embodiments, the neurological disorder is asymptomatic neurocognitive impairment.

In some embodiments, the neurological disorder is minor neurocognitive disorder.

In some embodiments, the neurological disorder is minor cognitive motor disorder.

In some embodiments, the neurological disorder is vacuolar myelopathy.

In some embodiments, the neurological disorder is peripheral neuropathy.

In some embodiments, the neurological disorder is polymyositis.

The association of a compound, or a pharmaceutically acceptable salt thereof, described herein and an antiviral agent in a composition may be physical or non-physical. Examples of physically associated compositions include: compositions (e.g. unitary formulations) comprising a compound, or pharmaceutically acceptable salt thereof, described herein and an antiviral agent in admixture (for example within the same unit dose); compositions comprising material in which a compound, or pharmaceutically acceptable salt thereof, described herein and an antiviral agent are chemically/physicochemically linked (for example by crosslinking, molecular agglomeration or binding to a common vehicle moiety); compositions comprising material in which a compound, or pharmaceutically acceptable salt thereof, described herein and an antiviral agent are chemically/physicochemically co-packaged (for example, disposed on or within lipid vesicles, particles (e.g. micro- or nanoparticles) or emulsion droplets); and pharmaceutical kits, pharmaceutical packs or patient packs in which a compound, or pharmaceutically acceptable salt thereof, described herein and an antiviral agent are co-packaged or co-presented (e.g. as part of an array of unit doses).

Examples of non-physically associated compositions include: material (e.g. a non-unitary formulation) comprising a compound, or pharmaceutically acceptable salt thereof, described herein or an antiviral agent together with instructions for the extemporaneous association of the compound, or pharmaceutically acceptable salt thereof, described herein and the antiviral agent to form a physical association of the two; material (e.g. a non-unitary formulation) comprising a compound, or pharmaceutically acceptable salt thereof, described herein or an antiviral agent together with instructions for adjunctive therapy with the compound, or pharmaceutically acceptable salt thereof, described herein and the antiviral agent; material comprising a compound, or pharmaceutically acceptable salt thereof, described herein or an antiviral agent with instructions for administration to a patient population in which the other of the compound, or pharmaceutically acceptable salt thereof, described herein or the antiviral agent have been (or are being) administered; and material comprising a compound, or pharmaceutically acceptable salt thereof, described herein or an antiviral agent in an amount or in a form which is specifically adapted for use in combination with the other of the compound, or pharmaceutically acceptable salt thereof, described herein or the antiviral.

Also provided are packaged compositions. Such packaged compositions include a pharmaceutical composition comprising at least one compound, or pharmaceutically acceptable salt thereof, described herein and/or the antiviral agent and instructions for using the composition to treat a subject (typically a human patient). In some embodiments, the instructions are for using the pharmaceutical composition to treat a subject suffering an HIV-related disorder. In some embodiments, the instructions are for using the pharmaceutical composition to treat a subject suffering an HIV-related neurological disorder. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In some embodiments, the compound of Formula I, or a pharmaceutically acceptable salt thereof, described herein and the antiviral agent are: a) in admixture; b) chemically/physicochemically linked; c) chemically/physicochemically co-packaged; or d) unmixed but co-packaged or co-presented.

In some embodiments, the compound of Formula I, or a pharmaceutically acceptable salt thereof, described herein and the antiviral agent are in admixture.

In some embodiments, the compound of Formula I, or a pharmaceutically acceptable salt thereof, described herein and the antiviral agent are chemically/physicochemically linked.

In some embodiments, the compound of Formula I, or a pharmaceutically acceptable salt thereof, described herein and the antiviral agent are chemically/physicochemically co-packaged.

In some embodiments, the compound of Formula I, or a pharmaceutically acceptable salt thereof, described herein and the antiviral agent are unmixed but co-packaged or co-presented.

In some embodiments, the compound of Formula I, or a pharmaceutically acceptable salt thereof, described herein and the antiviral agent are co-packaged in a single container or in a plurality of containers within a single outer package.

In some embodiments, the compound of Formula I, or a pharmaceutically acceptable salt thereof, described herein is administered before the antiviral agent.

In some embodiments, the compound of Formula I, or a pharmaceutically acceptable salt thereof, described herein is administered after the antiviral agent.

In some embodiments, the compound of Formula I, or a pharmaceutically acceptable salt thereof, described herein and the antiviral agent are administered simultaneously.

In some embodiments, the antiviral agent and the compound of Formula I, or a pharmaceutically acceptable salt thereof, described herein, are administered simultaneously in a unitary formulation.

In some embodiments, the antiviral agent and the compound of Formula I, or a pharmaceutically acceptable salt thereof, described herein, are administered simultaneously in different formulations.

In some embodiments, the antiviral agent and the compound of Formula I or a pharmaceutically acceptable salt thereof, described herein are in a co-packaged drug product.

In general, the compound, or pharmaceutically acceptable salt thereof, described herein and the antiviral agent will be administered in therapeutically effective amounts by any of the accepted modes of administration for agents that serve similar utilities. The actual amounts of the compound, or pharmaceutically acceptable salt thereof, described herein and the antiviral agent, i.e., the active ingredients, will depend upon numerous factors such as the severity of the disease to be treated, the age and relative health of the subject, the potency of the compound used, the route and form of administration, and other factors well know to the skilled artisan. The active ingredients can be administered at least once a day, such as once or twice a day.

In some embodiments, the compound, or pharmaceutically acceptable salt thereof, described herein and/or the antiviral agent are administered as pharmaceutical compositions. Accordingly, provided are pharmaceutical compositions comprising a compound, or a pharmaceutically acceptable salt thereof, described herein and/or an antiviral agent, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or pharmaceutically acceptable salt thereof, described herein and/or the antiviral agent is sufficient to provide a practical quantity of material for administration per unit dose of the compound, or pharmaceutically acceptable salt thereof, described herein and/or the antiviral agent.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or pharmaceutically acceptable salt thereof, described herein and/or the antiviral agent.

Effective concentrations of the compound, or pharmaceutically acceptable salt thereof, described herein and/or the antiviral agent are mixed with a suitable pharmaceutically acceptable vehicle. In instances in which the compound, or pharmaceutically acceptable salt thereof, described herein and/or the antiviral agent exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of the compound, or pharmaceutically acceptable salt thereof, described herein and/or the antiviral agent, the resulting mixture may be a solution, suspension, emulsion or the like. The form of the resulting mixture depends upon a number of factors, including the intended mode of administration and the solubility of the compound, or pharmaceutically acceptable salt thereof, described herein and the antiviral agent in the chosen vehicle. The effective concentration sufficient for ameliorating the symptoms of the disease treated may be empirically determined.

The compound, or pharmaceutically acceptable salt thereof, described herein and the antiviral agent may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of a compound, or pharmaceutically acceptable salt thereof, described herein and/or the antiviral agent. In some embodiments, oral pharmaceutical compositions contain at least 5% (weight %) of a compound, or pharmaceutically acceptable salt thereof, described herein and/or the antiviral agent. Some embodiments contain from 25% to 50% or from 5% to 75% of a compound, or pharmaceutically acceptable salt thereof, described herein and/or the antiviral agent.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or pharmaceutically acceptable salt thereof, described herein and/or the antiviral agent can be incorporated into oral liquid preparations such as aqueous or oily suspensions, solutions, emulsions, syrups, or elixirs, for example. Moreover, pharmaceutical compositions containing a compound, or pharmaceutically acceptable salt thereof, described herein and/or an antiviral agent can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel RC-591, tragacanth and sodium alginate; typical wetting agents include lecithin and polysorbate 80; and typical preservatives include methyl paraben and sodium benzoate.

Aqueous suspensions contain the pharmaceutically acceptable salt thereof, described herein and/or the antiviral agent in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or pharmaceutically acceptable salt thereof, described herein and/or the antiviral agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or pharmaceutically acceptable salt thereof, described herein and/or the antiviral agent may be administered parenterally in a sterile medium. Parenteral administration includes subcutaneous injections, intravenous, intramuscular, intrathecal injection or infusion techniques. The compound, or pharmaceutically acceptable salt thereof, described herein and/or the antiviral agent, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or pharmaceutically acceptable salt thereof, described herein and/or the antiviral agent may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or pharmaceutically acceptable salt thereof, described herein and/or the antiviral agent may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or pharmaceutically acceptable salt thereof, described herein and/or the antiviral agent may also be formulated for transdermal administration as a transdermal patch.

Topical pharmaceutical compositions comprising at least one compound, or pharmaceutically acceptable salt thereof, described herein and/or the antiviral agent can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or pharmaceutically acceptable salt thereof, described herein and/or the antiviral agent may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound, or pharmaceutically acceptable salt thereof, described herein and/or the antiviral agent include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or pharmaceutically acceptable salt thereof, described herein and/or the antiviral agent. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of the compound, or pharmaceutically acceptable salt thereof, described herein and/or the antiviral agent. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

In all of the foregoing the compound, or pharmaceutically acceptable salt thereof, described herein and/or the antiviral agent can be administered in combination with other active agents.

When used in combination with one or more additional pharmaceutical agent or agents, the compound, or pharmaceutically acceptable salt thereof, described herein and/or the antiviral agent may be administered prior to, concurrently with, or following administration of the additional pharmaceutical agent or agents.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or pharmaceutically acceptable salt thereof, described herein and the antiviral agent are typically administered at dosage levels and in a manner customary for KMO inhibitors and antiviral agents respectively. For example, the compound, or pharmaceutically acceptable salt thereof, described herein and/or the antiviral agent can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of a compound, or pharmaceutically acceptable salt thereof, described herein and/or an antiviral agent for example, 0.1-50 mg of at least one compound, or pharmaceutically acceptable salt thereof, described herein and/or an antiviral agent. For intravenous administration, the at least one compound, or pharmaceutically acceptable salt thereof, described herein and/or an antiviral agent can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of a compound, or pharmaceutically acceptable salt thereof, described herein and/or an antiviral agent.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds, pharmaceutically acceptable salts and prodrugs thereof, described herein, compositions, and methods described herein are further illustrated by the following non-limiting examples.

As used herein, the following abbreviations have the following meanings. If an abbreviation is not defined, it has its generally accepted meaning.

DCM=dichloromethane
DMF=N,N-dimethylformamide
DMSO=dimethylsulfoxide
EtOAc=ethyl acetate
g=gram
hr=hour
hrs=hours
LC/MS=liquid chromatography/mass spectrometry
mg=milligram
min=minutes
mL=milliliter
mmol=millimoles
mM=millimolar
nm=nanometer
rt=room temperature
TBME=t-butyl methyl ether
THF=tetrahydrofuran
μL=microliter
μM=micromolar
1 g/1 mL=1 vol Experimental Commercially available reagents and solvents (HPLC grade) were used without further purification.

Thin-layer chromatography (TLC) analysis was performed with Kieselgel 60 $F_{254}$ (Merck) plates and visualized using UV light. Microwave reactions were carried out using CEM focused microwaves.

Analytical HPLC-MS was performed on Agilent HP1100 and Shimadzu 2010, systems using reverse phase Atlantis dC18 columns (5 μm, 2.1×50 mm), gradient 5-100% B (A=water/0.1% formic acid, B=acetonitrile/0.1% formic acid) over 3 minutes, injection volume 3 μL, flow=1.0 mL/min. UV spectra were recorded at 215 nm using a Waters 2487 dual wavelength UV detector or the Shimadzu 2010 system. Mass spectra were obtained over the range m/z 150 to 850 at a sampling rate of 2 scans per second using Waters ZMD and over m/z 100 to 1000 at a sampling rate of 2 Hz using Electrospray Ionisation, by a Shimadzu 2010 LC-MS system, or analytical HPLC-MS was performed on Agilent HP1100 and Shimadzu 2010, systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 µL, flow=0.6 mL/min. UV spectra were recorded at 215 nm using a Waters 2996 photo diode array or on the Shimadzu 2010 system. Mass spectra were obtained over the range m/z 150 to 850 at a sampling rate of 2 scans per second using Waters ZQ and over m/z 100 to 1000 at a sampling rate of 2 Hz using Electrospray Ionisation, by a Shimadzu 2010 LC-MS system. Data were integrated and reported using OpenLynx and OpenLynx Browser software or via Shimadzu Psi Port software.

Example 1

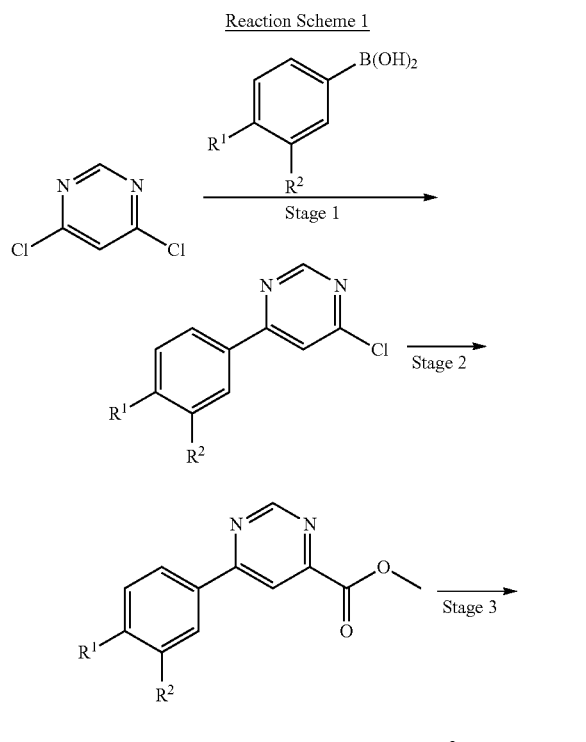

Referring to Reaction Scheme 1, Stage 1, to a stirred suspension of dichloropyrimidine (1 eq) in 1,4-dioxane (15 vol) was added boronic acid (0.7 eq) and Pd(PPh$_3$)$_4$ (0.025 eq). A 2 M K$_2$CO$_3$ solution (7.5 vol) was added to the resulting mixture, which was heated at 90° C. overnight under an atmosphere of N$_2$. The reaction mixture was cooled to room temperature and concentrated in vacuo. The residue was dissolved in EtOAc:water (1:1) (100 vol) and the resulting solution filtered through celite. The organic layer was separated and the aqueous layer further extracted with EtOAc (50 vol). The combined organic layers were washed with saturated aqueous NaCl (20 vol), dried over Na$_2$SO$_4$, filtered and the solvent removed in vacuo. The resulting residue was purified by flash column chromatography (eluent: [0:1 to 1:19] EtOAc:heptane) to afford the required target compounds.

Referring to Reaction Scheme 1, Stage 2, 4-chloro-6-substituted-phenyl-pyrimidine (1 eq), PdCl$_2$(dppf).DCM (0.05 eq) and triethylamine (2 eq) were suspended in degassed MeOH (50 vol) in a bomb fitted with a magnetic stirrer bar. The atmosphere in the reaction vessel was replaced with N$_2$ by successive evacuation and charging with N$_2$ gas (this process was repeated three times). The bomb was then flushed with CO by successive charging with CO and evacuation. The vessel was pressurized to 5 bar of CO and heated at 50° C. with stirring for 5 hours. The reaction vessel was allowed to cool to room temperature before venting CO and flushing with N$_2$. The reaction mixture was concentrated in vacuo and the resulting residue dissolved in EtOAc (30 vol) and water (30 vol). The solution was filtered through cotton wool and the organic layer was separated, washed with saturated aqueous NaCl (15 vol), dried over Na$_2$SO$_4$, filtered and concentrated under reduced pressure. Purification by flash column chromatography (eluent: [0:1 to 1:9] EtOAc:heptane) yielded the target compounds.

Referring to Reaction Scheme 1, Stage 3, 6-substituted-phenyl-pyrimidine-4-carboxylic acid methyl ester (1 eq) was suspended in MeOH (20 vol), 1 M NaOH solution (20 vol) and stirred at room temperature for 4 hours. The reaction mixture was acidified with 2 M HCl. Soluble products were extracted with DCM (2×20 vol) and the combined organic layers were dried over MgSO$_4$, filtered and concentration under reduced pressure afforded the target compounds. Insoluble products were filtered, washed with water (3×10 vol) and heptane (3×10 vol) before drying in vacuo to yield the target compounds.

The following compounds were prepared substantially as described above.

| Compound No. | Chemical Structure | Molecular Weight | Mass Spec Result |
|---|---|---|---|
| 1 | 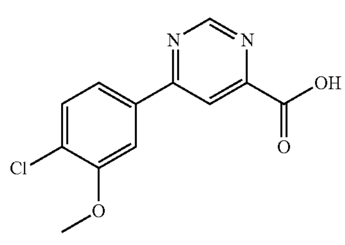 [SMILES: COc1cc(-c2cc(C(=O)O)ncn2)ccc1Cl] | 264.67 | [M + H]$^+$ = 265/267, 100% @ rt = 3.53 and 3.70 min |

-continued

| Compound No. | Chemical Structure | Molecular Weight | Mass Spec Result |
|---|---|---|---|
| 16 | pyrimidine-4-carboxylic acid with 4-chloro-3-fluorophenyl | 252.63 | [M + H]⁺ = 253, 100% @ rt = 4.06 min |
| 17 | pyrimidine-4-carboxylic acid with 3-chloro-4-fluorophenyl | 252.63 | [M + H]⁺ = 253, 100% @ rt = 3.92-4.23 |
| 18 | pyrimidine-4-carboxylic acid with 3,4-dichlorophenyl | 269.09 | [M + H]⁺ = 269, 100% @ rt = 4.04 min |
| 19 | pyrimidine-4-carboxylic acid with 3,4-difluorophenyl | 236.18 | [M + H]⁺ = 237, 100% @ rt = 3.74 min |
| 20 | pyrimidine-4-carboxylic acid with 3-chloro-4-methoxyphenyl | 264.67 | [M + H]⁺ = 265, 100% @ rt = 3.73-4.10 |

Example 2

Reaction Scheme 2

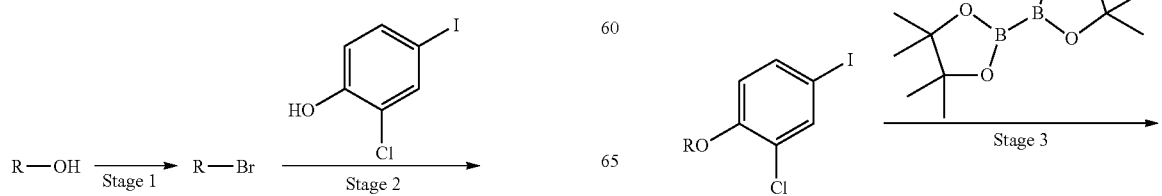

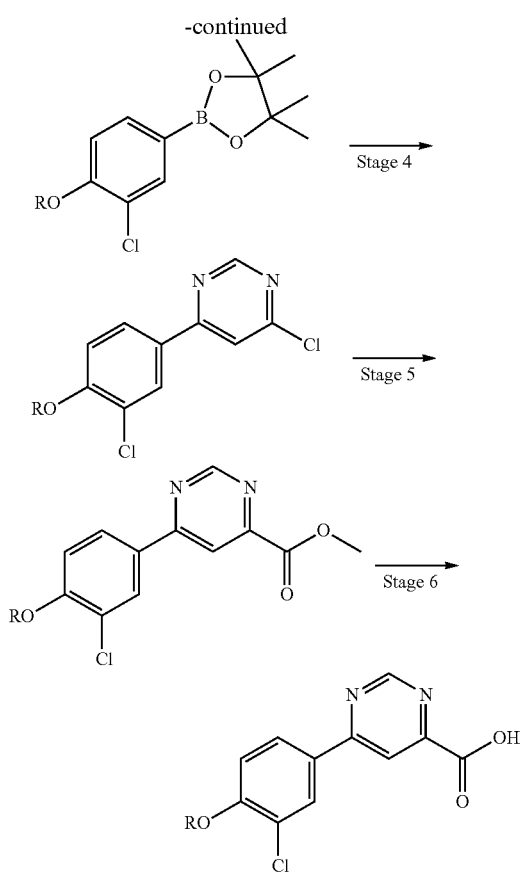

Referring to Reaction Scheme 2, Stage 1, R—OH (1 eq) in DCM (70 vol) at 0° C. was added dibromo triphenyl phosphorane (1.2 eq). The reaction mixture was allowed to warm to room temperature and stirred for 16 hrs. The solvent removed in vacuum. DCM (10 vol) was added to the reaction mixture. The precipitate was filtered to afford the target compound. The crude mixture was used in the next step without further purification.

Referring to Reaction Scheme 2, Stage 2, R—Br (1.1 eq) in DMF (15 vol) were added 2-chloro-4-iodophenol (1 eq) and $Cs_2CO_3$ (2.5 eq). The reaction mixture was refluxed for 3 hours under nitrogen. The reaction mixture was allowed to cool to room temperature and EtOAc (40 vol) and aq ammonia (40 vol) were added. The organic layer was separated and the aqueous layer further extracted with EtOAc (50 vol). The combined organic layers were washed with saturated aqueous NaCl (20 vol), dried over $Na_2CO_3$, filtered and the solvent removed in vacuo. The resulting residue was purified by flash column chromatography (eluent: [3:1] EtOAc:heptane) to afford the required target compound.

Referring to Reaction Scheme 2, Stage 3, to a stirred suspension of 4-substituted-3-chloro-iodobenzene (1 eq) in degassed DMF (15 vol) was added bis-diborane (1.05 eq), $Pd(OAc)_2$ (0.04 eq) and KOAc (3.0 eq). The reaction mixture was heated at 90° C. for 5 hrs under an atmosphere of $N_2$. The reaction mixture was cooled to room temperature and filtered through celite then concentrated in vacuo to give crude product. Crude was used in the next step without further purification.

Referring to Reaction Scheme 2, Stage 4, to a stirred suspension of dichloropyrimidine (1 eq) in 1,4-dioxane (90 vol) was added boronic ester (1.0 eq) and $Pd(PPh_3)_4$ (0.03 eq). A 2 M $K_2CO_3$ (3 eq) solution was added to the resulting mixture, which was heated at 90° C. for 16 hrs under an atmosphere of $N_2$. The reaction mixture was cooled to room temperature and concentrated in vacuo. The residue was dissolved in EtOAc:water (1:1) (100 vol) and the resulting solution filtered through celite. The organic layer was separated and the aqueous layer further extracted with EtOAc (50 vol). The combined organic layers were washed with saturated aqueous NaCl (20 vol), dried over $Na_2SO_4$, filtered and the solvent removed in vacuo. The resulting residue was purified by flash column chromatography (eluent: [3:1] EtOAc:heptane) to afford the required target compound.

Referring to Reaction Scheme 2, Stage 5, 4-chloro-6-substituted-phenyl-pyrimidine (1 eq), $PdCl_2(dppf).DCM$ (0.05 eq) and triethylamine (2 eq) were suspended in degassed MeOH (50 vol) in a bomb fitted with a magnetic stirrer bar. The atmosphere in the reaction vessel was replaced with $N_2$ by successive evacuation and charging with $N_2$ gas (this process was repeated three times). The bomb was then flushed with CO by successive charging with CO and evacuation. The vessel was pressurized to 5 bar of CO and heated at 50° C. with stirring for 16 hours. The reaction vessel was allowed to cool to room temperature before venting CO and flushing with $N_2$. The reaction mixture was concentrated in vacuo and the resulting residue dissolved in EtOAc (30 vol) and water (30 vol). The organic layer was separated, washed with saturated aqueous NaCl (15 vol), dried over $Na_2SO_4$, filtered and concentrated under reduced pressure. Purification by re-crystallization using MeOH yielded the target compound.

Referring to Reaction Scheme 2, Stage 6, 6-substituted-phenyl-pyrimidine-4-carboxylic acid methyl ester (1 eq) was suspended in THF (20 vol), 2 M NaOH (2.5 eq) and stirred at room temperature for 4 hours. Solvent (THF) was removed and reaction mixture was acidified with 2 M HCl. Resulting solid was filtered and was with water to give desired product.

The following compounds were prepared substantially as described above.

| Compound No. | Chemical Structure | Molecular Weight | Mass Spec Result |
|---|---|---|---|
| 2 | 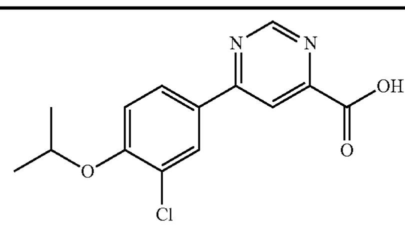 | 292.72 | $[M + H]^+$ = 293/295, 100% @ rt = 4.18 min |

-continued

| Compound No. | Chemical Structure | Molecular Weight | Mass Spec Result |
|---|---|---|---|
| 3 | 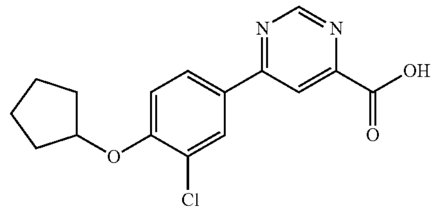 [SMILES: O=C(O)c1cc(-c2ccc(OC3CCCC3)c(Cl)c2)ncn1] | 318.76 | $[M + H]^+ = 319$, 100% @ rt = 4.61 min |
| 4 | 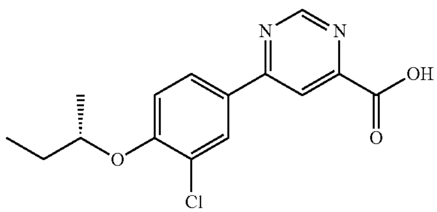 [SMILES: CC[C@H](C)Oc1ccc(-c2cc(C(=O)O)ncn2)cc1Cl] | 306.75 | $[M + H]^+ = 307/309$, 100% @ rt = 4.37 min |
| 5 | 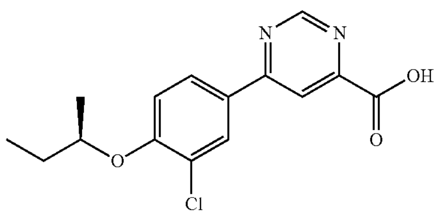 [SMILES: CC[C@@H](C)Oc1ccc(-c2cc(C(=O)O)ncn2)cc1Cl] | 306.75 | $[M + H]^+ = 307/309$, 100% @ rt = 4.37 min |
| 6 | 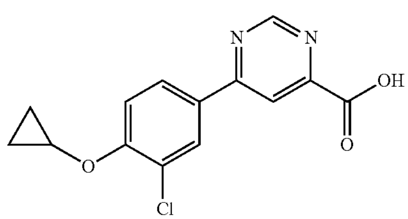 [SMILES: O=C(O)c1cc(-c2ccc(OC3CC3)c(Cl)c2)ncn1] | 290.71 | $[M + H]^+ = 291/293$, 100% @ rt = 3.93 min |
| 7 | 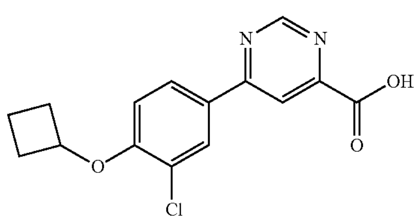 [SMILES: O=C(O)c1cc(-c2ccc(OC3CCC3)c(Cl)c2)ncn1] | 304.79 | $[M + H]^+ = 305/307$, 100% @ rt = 4.20 min |
| 8 | 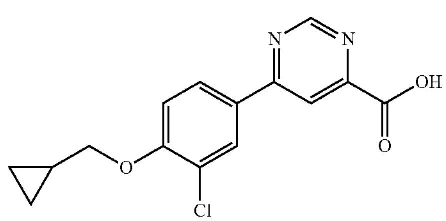 [SMILES: O=C(O)c1cc(-c2ccc(OCC3CC3)c(Cl)c2)ncn1] | 302.72 | $[M - Na]^- = 303/305$, 100% @ rt = 4.14 min |

Example 3

Reaction Scheme 3

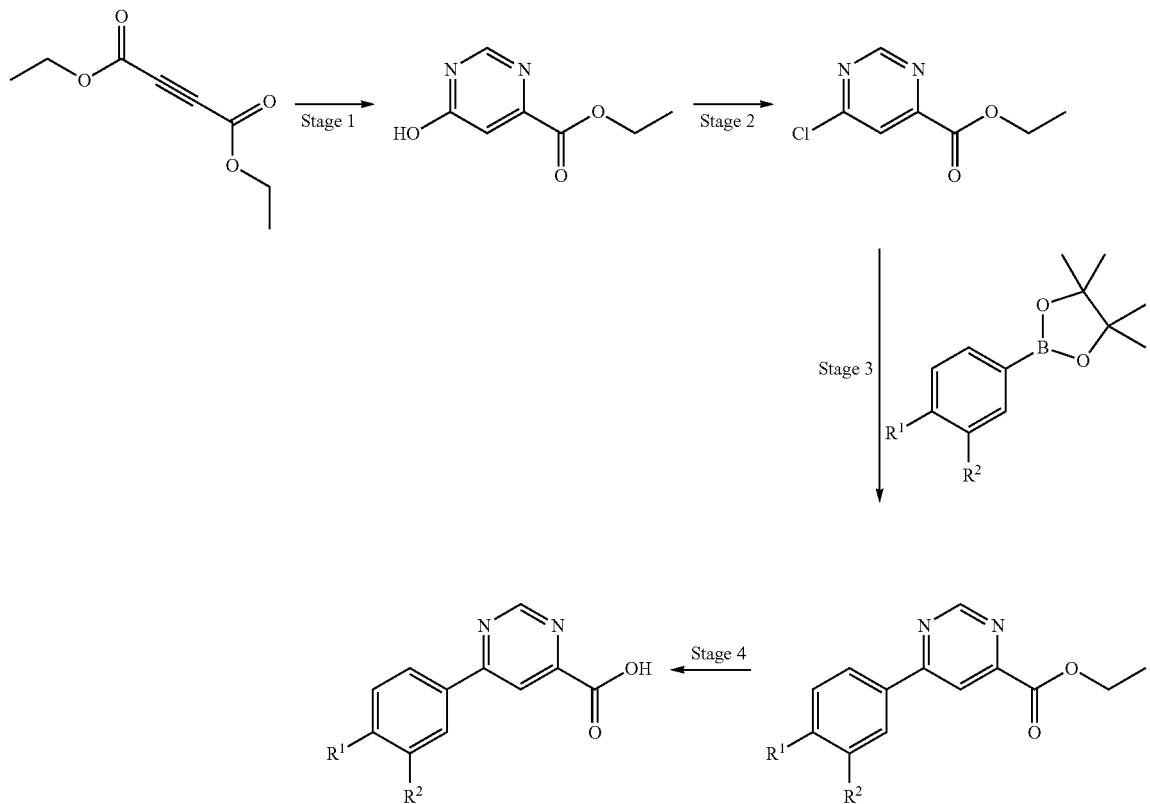

Referring to Reaction Scheme 3, Stage 1. Triethylamine (19.01 mL, 146.92 mmol) was added dropwise to a solution of diethyl but-2-ynedioate (25.0 g, 146.92 mmol) and formamidine hydrochloride (11.83 g, 146.92 mmol) in acetonitrile (500 mL). The resulting red solution was heated at 80° C. for 2.5 hours. After this time the reaction mixture was cooled to 5° C. using a saturated NaCl/ice bath and the reaction was stirred at this temperature for 25 minutes. After this time the resulting solid precipitate was collected under suction and dried on a sinter funnel for 30 minutes under vacuum at room temperature before drying in the vacuum oven at room temperature for 3 hours to give the desired compound (21.3 g, 86% yield) as a pale brown solid. Tr=0.85 min (3.5 minute method) m/z (ES+) [M+H]$^+$169.

Referring to Reaction Scheme 3, Stage 2. Ethyl 6-hydroxypyrimidine-4-carboxylate (21.3 g, 126.67 mmol) was dissolved in dry DMF (100 mL) in a 2 neck flask. The flask was purged with a stream of nitrogen while cooling in an ice bath for 10 minutes. After this time, thionyl chloride (15.6 mL, 215.6 mmol) was added dropwise over 20 minutes, before being warmed to room temperature and stirred under a nitrogen atmosphere for 2 hours. After this time, the reaction mixture was carefully poured onto ~100 mL ice water. TBME (100 mL) was added, the organic layer was separated and the aqueous extracted with further TBME (3×100 mL). The combined organic layers were washed consecutively with water (2×100 mL), and brine (100 mL) before being dried (MgSO$_4$), filtered and concentrated to give the desired compound (8.8 g, 37% yield) as a light orange powder. δH (500 MHz, DMSO) 9.23 (d, J=0.95 Hz, 1H), 8.16 (d, J=1.10 Hz, 1H), 4.39 (q, J=7.09 Hz, 2H), 1.34 (t, J=7.17 Hz, 3H). Tr=1.43 min (3.5 minute method) m/z (ES+) [M+H]$^+$187

Referring to Reaction Scheme 3, Stage 3. Tripotassium phosphate (1.12 g, 5.63 mmol) was added in one portion to a stirred solution of the dioxaborolane (3.75 mmol) and ethyl 6-chloropyrimidine-4-carboxylate (0.7 g, 3.75 mmol) in DMF (20 mL). The mixture was degassed with nitrogen for 5 minutes, after which time Pd(dppf)$_2$Cl$_2$ (0.14 g, 0.19 mmol) was added in one portion, the mixture was then heated to 80° C. and stirred at this temperature for 16 hours under a nitrogen atmosphere. After this time the reaction mixture was cooled to room temperature and partitioned between ethyl acetate (200 mL) and water (100 mL). The organic layer was separated, washed sequentially with water (100 mL) then brine (100 mL) before being dried (MgSO$_4$), filtered and concentrated. The resulting brown solid was purified by flash column chromatography (elution: 40% EtOAc, 60% Heptane) to give the desired compound.

Referring to Reaction Scheme 3, Stage 4. NaOH (2 M solution, 0.63 mL, 1.27 mmol) was added in one portion to a stirred solution of ethyl 6-substituted pyrimidine-4-carboxylate (1.15 mmol) in THF (10 mL) and the mixture was stirred at room temperature for 16 hours before being heated to reflux for 2 hours. After this time, the reaction mixture was cooled to room temperature and the resulting precipitate was collected by filtration, washed with THF (20 mL) before being dried under vacuum to give the desired compound.

The following compounds were prepared substantially as described above.

| Compound No. | Chemical Structure | Molecular Weight | Mass Spec Result |
|---|---|---|---|
| 9 | 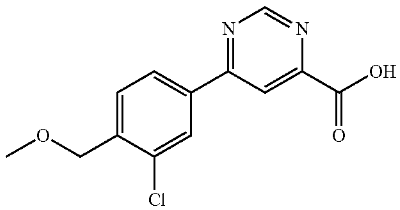 [SMILES: COCc1ccc(-c2cc(C(=O)O)ncn2)cc1Cl] | 278.04 | [M + H]⁺ = 279/281, 100% @ rt = 3.65 min |

Example 4

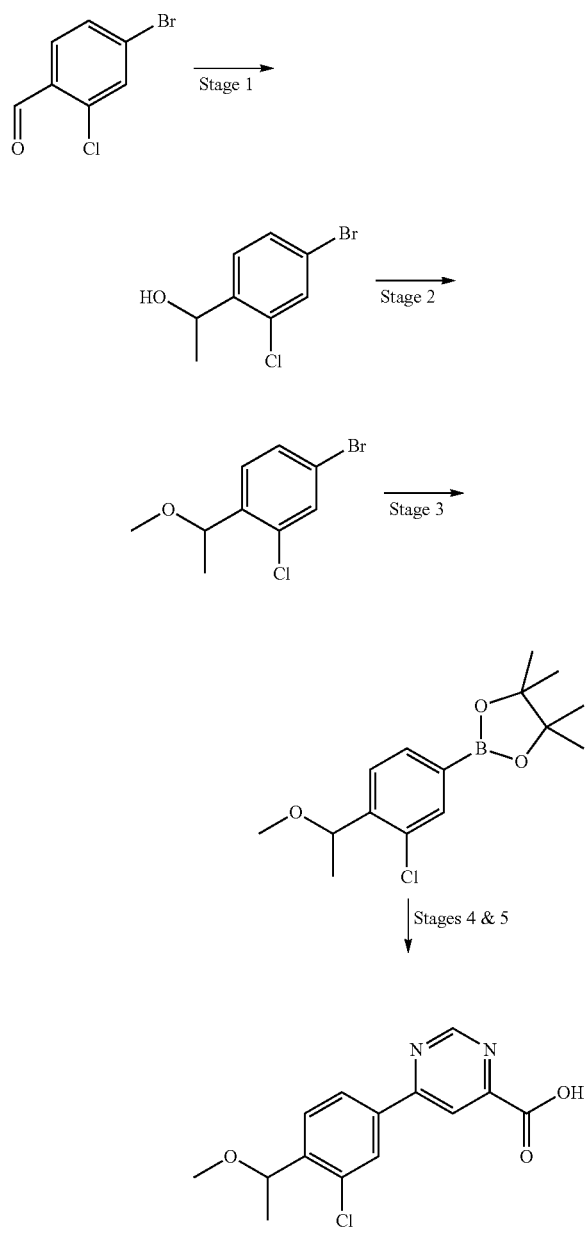

Reaction Scheme 4

Referring to Reaction Scheme 4, Stage 1. Methylmagnesium bromide (1.4M in toluene/THF, 1.5 mL, 0.046 mol) was added drop wise over 1 hour to a cold (−78° C.), stirred solution of 4-bromo-2-chlorobenzaldehyde (5.0 g, 0.023 mol) in THF (100 mL) and the mixture was stirred at this temperature under a nitrogen atmosphere for 1 hour. After this time, the reaction mixture was allowed to warm to room temperature over 1 hour before being stirred for a further 1.5 hours. The reaction mixture was then cooled to 5° C. in an ice bath and stirred for 10 minutes before saturated ammonium chloride (40 mL) was added drop wise and stirring continued at this temperature for a further 10 minutes before being allowed to warm to room temperature. The resulting mixture was then extracted with ethyl acetate (1×100 mL), the organic layer was washed sequentially with water (100 mL), and brine (100 mL) before being dried (MgSO$_4$), filtered and concentrated. The resulting residue was purified by flash column chromatography (elution: 10% ethyl acetate, 90% heptanes) to give the desired compound (4.33 g, 81% yield) as a colourless oil. δH (500 MHz, DMSO) 7.64 (d, J=1.58 Hz, 1H) 7.49-7.60 (m, 2H) 5.47 (d, J=3.00 Hz, 1H) 4.96 (dd, J=6.07, 2.60 Hz, 1H) 1.28 (d, J=6.31 Hz, 3H).

Referring to Reaction Scheme 4, Stage 2. Sodium hydride (60% in oil, 0.38 g, 9.6 mmol) was added portion wise over 5 minutes to a cooled (0° C.), stirred solution of 1-(4-bromo-2-chlorophenyl)ethan-1-ol (1.5 g, 6.4 mmol) in DMF (15 mL) and the reaction was stirred at this temperature for 20 minutes under a nitrogen atmosphere. After this time, methyl iodide (0.48 mL, 7.6 mmol) was added in one portion and the reaction mixture was allowed to warm to room temperature before being stirred for a further 18 hours. The reaction was quenched by the drop wise addition of water (15 mL) over 10 minutes and the resulting solution was extracted with ethyl acetate (2×30 mL). The combined organic extracts were washed sequentially with water (100 mL) and brine (10 mL) before being dried (MgSO$_4$), filtered and concentrated to give the desired compound (1.5 g, 99% yield) as a yellow oil. δH (500 MHz, DMSO) 7.71 (d, J=1.89 Hz, 1H) 7.60 (dd, J=8.35, 1.89 Hz, 1H) 7.39 (d, J=8.35 Hz, 1H) 4.63 (q, J=6.46 Hz, 1H) 3.16 (s, 3H) 1.26-1.38 (m, 3H).

Referring to Reaction Scheme 4, Stages 3, 4 & 5 were carried out as described in Reaction Scheme 3

The following compounds were prepared substantially as described above.

| Compound No. | Chemical Structure | Molecular Weight | Mass Spec Result |
|---|---|---|---|
| 10 | 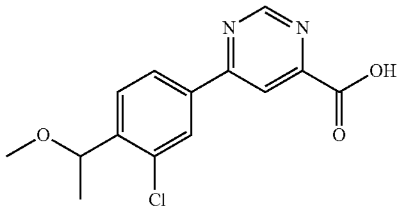 [SMILES: COC(C)c1ccc(-c2cc(C(=O)O)ncn2)cc1Cl] | 292.72 | [M + H]⁺ = 293/295, 100% @ rt = 3.72 min |

Example 5

The following compounds may be prepared substantially as described above.

| Compound No. | Chemical Structure | Chemical Name |
|---|---|---|
| 11 | 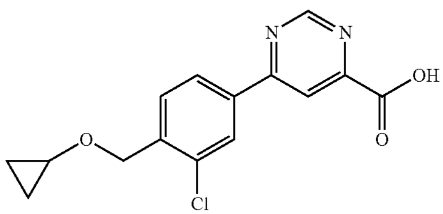 [SMILES: O=C(O)c1cc(-c2ccc(COC3CC3)c(Cl)c2)ncn1] | 6-(3-chloro-4-(cyclopropoxymethyl)-phenyl)pyrimidine-4-carboxylic acid |
| 12 | 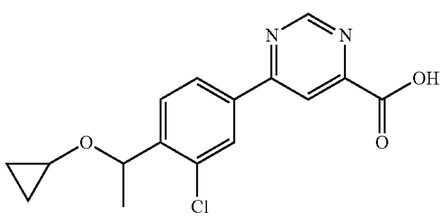 [SMILES: CC(OC1CC1)c1ccc(-c2cc(C(=O)O)ncn2)cc1Cl] | 6-(3-chloro-4-(1-cyclopropoxyethyl)-phenyl)pyrimidine-4-carboxylic acid |
| 13 | 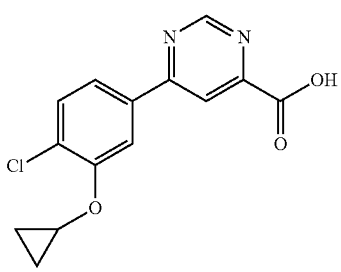 [SMILES: O=C(O)c1cc(-c2ccc(Cl)c(OC3CC3)c2)ncn1] | 6-(4-chloro-3-cyclopropoxy-phenyl)pyrimidine-4-carboxylic acid |
| 14 | 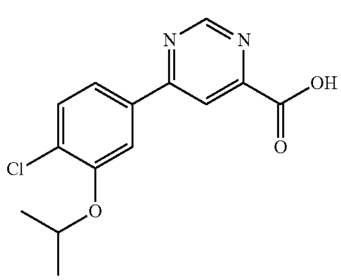 [SMILES: CC(C)Oc1cc(-c2cc(C(=O)O)ncn2)ccc1Cl] | 6-(4-chloro-3-isopropoxy-phenyl)pyrimidine-4-carboxylic acid |

| Compound No. | Chemical Structure | Chemical Name |
|---|---|---|
| 15 | 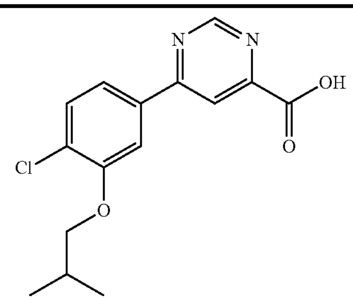 | 6-(4-chloro-3-isobutoxy-phenyl)pyrimidine-4-carboxylic acid |

Example 6

A generalized procedure for monitoring L-Kynurenine (KYN) hydroxylation to form product 3-Hydroxy-Kynurenine (3OH—KYN) by LC/MS is described below. Product is quantified by multiple reaction monitoring using MS.
Key Reagents:
Compound: Stock concentrations: 10 mM in 100% DMSO
Cell line: CHO GST HIS KMO cell line, 1E4 cells/well/100 µL in 96 well cell plate
Substrate: L-Kynurenine (Sigma: Cat#K3750, stock concentration:
  10 mM in 100 mM potassium phosphate buffer, pH 7.4)
Assay Conditions:
Medium: OptiMem (Reduced Serum Medium Ix, +L-Glutamine +
  HEPES-Phenol Red; GIBCO: Cat#11058)
Assay Volume: 200 µL
Plate Format: 96 well plate, transparent (Corning)
Read-Out: product (3OH—KYN) quantification using product specific MRM
Reader: LC/MS/MS
Assay Protocol:
  prepare serial dilution (factor 3) of compound in 100% DMSO (top concentration=6.67 mM, 100% DMSO)
  [8 points: 6.67 mM; 2.22 mM; 0.74 mM; 0.247 mM; 0.082 mM; 0.027 mM; 0.009 mM; 0.003 mM]
  prepare 300-fold concentrated solution of each compound concentration (top concentration 22.22 µM, 0.3% DMSO) in OptiMem medium
  [22.2 µM; 7.41 µM; 2.47 µM; 0.82 µM; 0.27 µM; 0.09 µM; 0.03 µM; 0.01 µM]
  prepare substrate (10 mM) at concentration of 1.1 mM in medium
  medium of cell plate is drawed off
  cells are washed with OptiMem (100 µL/well) and drawed off again
  assay mix: 90 µL OptiMem/well+90 µL compound/well of each concentration
  [final compound top concentration: 10 µM; 0.15% DMSO]
  [final compound bottom concentration: 0.004 µM; 0.15% DMSO]
  pre-incubation: 30 min at 37° C.
  add 20 µL/well of the 1.1 mM substrate solution (final assay concentration: 100 µM)
  positive control: 200 µL OptiMem
  negative control: 180 µL OptiMem+20 µL 1.1 mM substrate
  incubate ~24 h at 37° C.
  transfer 100 µL of each well in a transparent 96 well plate (Corning)
  add 100 µL/well 10% trichloro acetic acid (TCA) in water
  centrifugate plate for 3 min at 4000 rpm
  detect product by LC/MS (injection of 50 µL/well; 2.5 fold overfill of the 20 µL sample loop)
Data Analysis:
  $IC_{50}$'s are calculated using automated fitting algorithm (A+ Analysis)

Example 7

A method of monitoring L-Kynurenine (KYN) hydroxylation to form product 3-Hydroxy-Kynurenine (3OH—KYN) by LC/MS is described below. Product is quantified by multiple reaction monitoring.
Key Reagents:
Compound: Stock concentrations: 10 mM in 100% DMSO
Enzyme: KMO enzyme prepared at Evotec via mitochondria isolation from CHO-GST HIS KMO cells
Substrate: L-Kynurenine (Sigma: Cat#K3750)
  [stock concentration: 10 mM in 100 mM potassium phosphate buffer, pH 7.4]
Assay Conditions:
Buffer: 100 mM potassium phosphate, pH 7.4, 200 µM NADPH, 0.4 U/ml G6P-DH (Glucose 6-phosphate dehydrogenase), 3 mM G6P (D-Glucose 6-phosphate)
Assay Volume: 40 µL
Plate Format: 384 well plate, transparent (Matrix)
Read-Out: product (3OH—KYN) quantification using product specific MRM
Reader: LC/MS/MS
Assay Protocol:
  prepare serial dilution (factor 3) of compound in 100% DMSO (top concentration=10 mM, 100% DMSO)
  [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
  [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µL compound/well of each concentration+24 µL assay buffer/well+8 µL KMO human enzyme+4 µL 1 mM substrate (final concentration=100 µM)
  [final compound top concentration: 30 µM; 0.3% DMSO]

[final compound bottom concentration: 0.0137 μM; 0.3% DMSO]
positive control: 4 μL 50 μM FCE28833 in assay buffer [0.5% DMSO] (final assay concentration=5 μM)+24 μL assay buffer/well+8 μL KMO human enzyme+4 μL 1 mM substrate (final concentration=100 μM)
negative control: 28 μL assay buffer/well+8 μL KMO human enzyme+4 μL 1 mM substrate (final concentration=100 μM)
incubate 400 min at RT
add 40 μL/well 10% trichloro acetic acid in water to stop the assay and precipitate protein
centrifuge plate for 3 min at 4000 rpm
product detection by LC/MS (injection of 50 μL/well; 2.5 fold overfill of the 20 μL sample loop)

Data Analysis:

$IC_{50}$'s are calculated using automated fitting algorithm (A+ Analysis).

Example 8

A method of monitoring L-Kynurenine (KYN) hydroxylation to form 3-Hydroxy-Kynurenine (3OH—KYN) by LC/MS is described. Product is quantified by multiple reaction monitoring (MRM method).

Key Reagents:
Compound: Stock concentrations: 10 mM in 100% DMSO
Enzyme: KMO enzyme prepared at Evotec from mouse liver (4-6 weeks old) via mitochondria isolation as described in the literature
Substrate: L-Kynurenine (Sigma: Cat# K3750, stock concentration: 10 mM in 100 mM potassium phosphate buffer, pH 7.4)

Assay Conditions:
Buffer: 100 mM potassium phosphate, pH 7.4, 200 μM NADPH, 0.4 U/mL G6P-DH (Glucose 6-phosphate Dehydrogenase), 3 mM G6P (D-Glucose 6-phosphate)
Assay Volume: 40 μL
Plate Format: 384 well plate, transparent (Matrix)
Read-Out: product (3OH—KYN) quantification using product specific MRM
Reader: LC/MS/MS
Assay Protocol:
prepare serial dilution (factor 3) of compound in 100% DMSO (top concentration=10 mM, 100% DMSO)
[8 points: 10 mM; 3.33 mM; 1.11 mM; 0.37 mM; 0.12 mM; 0.04 mM; 0.0137 mM; 0.0045 mM, 0.0015 mM]
prepare 3.33-fold concentrated solution of each compound concentration (top concentration 300 μM, 3% DMSO) in assay buffer
[concentrations: 300 μM; 100 μM; 33.3 μM; 11.1 μM; 3.70 μM; 1.23 μM; 0.41 μM; 0.137 μM]
prepare substrate (10 mM) at concentration of 1 mM in assay buffer
assay mix: 4 μL compound/well of each concentration+24 μL assay buffer/well+8 μL KMO mouse enzyme+4 μL 1 mM substrate (final concentration=100 μM)
[final compound top concentration: 30 μM; 0.3% DMSO]
[final compound bottom concentration: 0.0137 μM; 0.3% DMSO]
positive control: 4 μL 50 μM FCE28833 in assay buffer, 0.5% DMSO [final assay concentration=5 μM]+24 μL assay buffer/well+8 μL KMO mouse enzyme+4 μL 1 mM substrate [final concentration=100 μM]
negative control: 28 μL assay buffer/well+8 μL KMO mouse enzyme+4 μL 1 mM substrate
[final concentration=100 μM]
incubate 40 min at RT
add 40 μL/well 10% trichloro acetic acid in water to stop the assay and precipitate protein
centrifuge plate for 3 min at 4000 rpm
product detection by LC/MS (injection of 20 μL/well, 2 fold overfill of the 10 μL sample loop)

Data Analysis:

$IC_{50}$'s are calculated using automated fitting algorithm (A+ Analysis).

Example 9

Using procedures similar to those described herein, the following compounds were assayed for activity.

| IUPAC name | % Inhibition at 10 μM* |
|---|---|
| 6-(4-chloro-3-methoxy-phenyl)pyrimidine-4-carboxylic acid | 99.62 |
| 6-(3-chloro-4-isopropoxy-phenyl)pyrimidine-4-carboxylic acid | 100 |
| 6-(3-chloro-4-(cyclopentyloxy)-phenyl)pyrimidine-4-carboxylic acid | 97 |
| (S)-6-(4-sec-butoxy-3-chloro-phenyl)pyrimidine-4-carboxylic acid | 100 |
| (R)-6-(4-sec-butoxy-3-chloro-phenyl)pyrimidine-4-carboxylic acid | 100 |
| 6-(3-chloro-4-cyclopropoxy-phenyl)pyrimidine-4-carboxylic acid | 100 |
| 6-(3-chloro-4-cyclobutoxy-phenyl)pyrimidine-4-carboxylic acid | 100 |
| 6-(3-chloro-4-(cyclopropylmethoxy)-phenyl)pyrimidine-4-carboxylic acid | 101 |
| 6-(4-chloro-3-fluoro-phenyl)pyrimidine-4-carboxylic acid | 102.645 |

Example 10

Microdialysis Procedure for Mouse Studies

Animals were anesthetized using isoflurane (2%, 800 mL/min O2). Bupivacain/epinephrine was used for local analgesia, finadyne or carprophen for peri-/post-operative analgesia. The animals were placed in a stereotaxic frame (Kopf instruments, USA). I-shaped probes (membrane: polyacrylonitrile, 3 mm exposed surface; Brainlink, the Netherlands) were inserted in the striatum. After surgery, animals were kept individually in cages; provided food and water ad libitum.

Experiments were performed one day after surgery. On the day of the experiment, the probes of the animals were connected with flexible PEEK tubing to a microperfusion pump (Harvard PHD 2000 Syringe pump, Holliston, Mass. or similar). The I-shaped microdialysis probes were perfused with aCSF containing 147 mM NaCl, 3.0 mM KCl, 1.2 mM CaCl2 and 1.2 mM MgCl2, at a flow rate of 1.5 μL/min. Microdialysis samples were collected at 20-minute intervals by an automated fraction collector (820 Microsampler, Univentor, Malta or similar) into mini-vials already containing 10 μL 0.02 M formic acid (FA) and 0.04% ascorbic acid in ultrapurified H2O. At t=−30 min vehicle or KMO inhibitor were be administered, to ensure central and peripheral inhibition of KMO at the time of administration of kynurenine. At t=0 vehicle or kynurenine were administered. Microdialysate samples were collected for 240 min after administration of kynurenine. All the dialysis samples were stored at −80° C. awaiting their analysis. Dialysate levels of any or all of KP metabolites KYN, KYNA, 3-OH—KYN, AA and QA were quantified by LC-MS/MS at by Brains On-Line. After the experiment, the mice were sacrificed and terminal brain (striatum+cortex), liver, kidney, plasma and CSF samples were collected for analysis of KP metabolites. Levels of KP metabolites were measured in terminal brain (striatum+cortex), liver, kidney, plasma and CSF samples at Brains On-Line. Finally, levels of kynurenine and KMO inhibitors in dose formulation samples were quantified by Brains On-Line.

Example 11

A method of examining the modulation of KYN, KYNA, AA, and 3-HK via KMO inhibition with Compound 6 in striatum extracellular space is disclosed. Specifically, this experiment is aimed at demonstrating the dose dependent differences in central KP metabolite (KYN, KYNA, AA, 3-HK) elevations between dosing of Compound 6 at various levels in an animal brain. Following the microdialysis procedure described herein, dialysate levels of KP metabolites KYN, KYNA, 3-HK, and AA were quantified by LC-MS/MS at by Brains On-Line.

Figure 2:
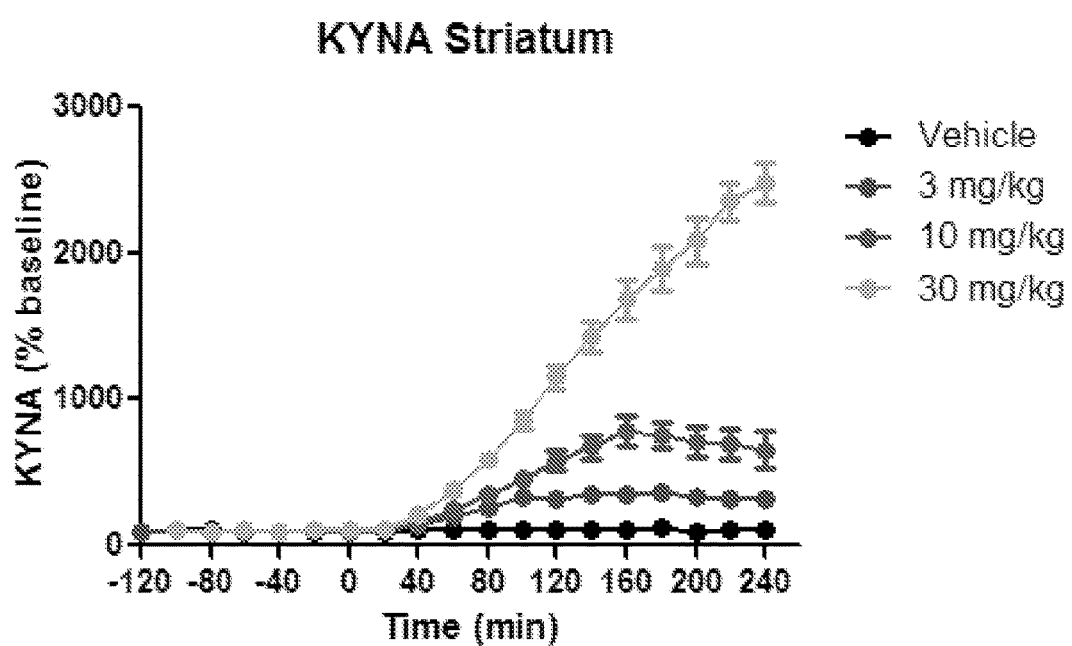
FIG. 2. shows the dose dependent increase of kynurenic acid (KYNA) in the striatum extracellular space following dosing of Compound 6.
Figure 3:
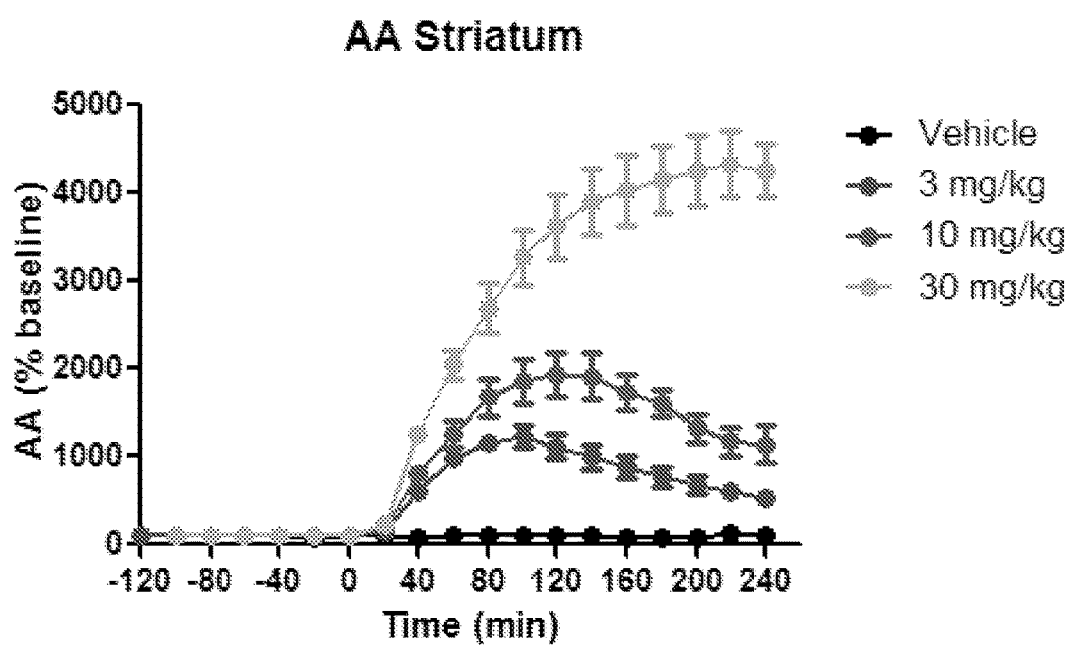
FIG. 3. shows the dose dependent increase of anthranilic acid (AA) in the striatum extracellular space following dosing of Compound 6.
Figure 4:
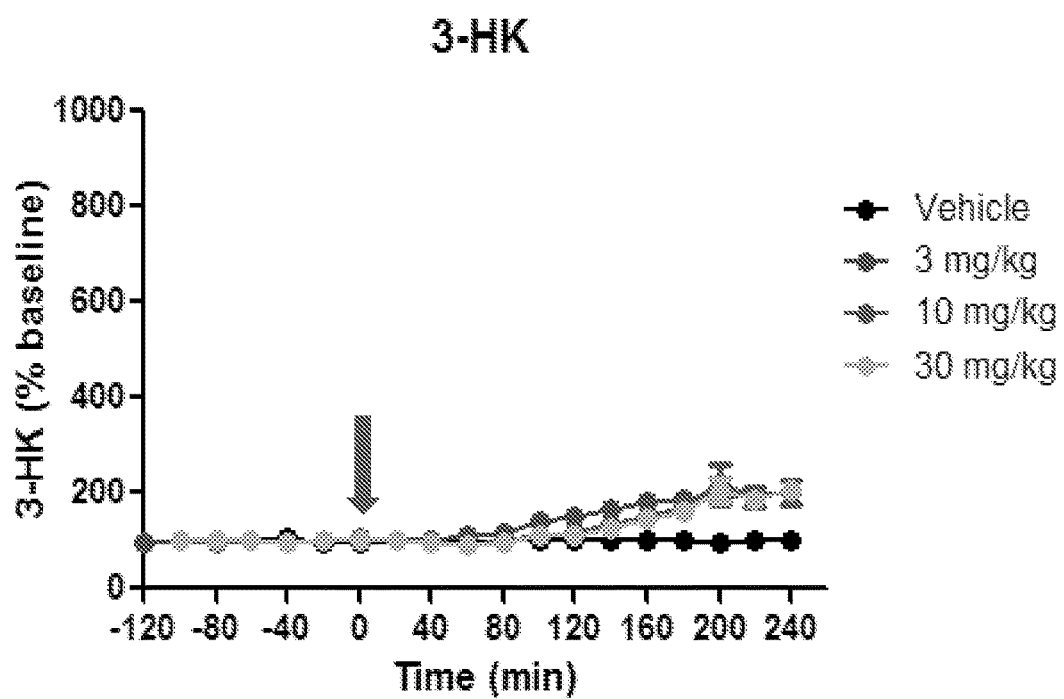
FIG. 4. shows insufficient modulation of 3-hydroxykynurenine (3-HK or 3-OH—KYN) in the striatum extracellular space following dosing of Compound 6.

When microdialysis after PO dosing Compound 6 at various dosage levels (3 mg/kg, 10 mg/kg, or 30 mg/kg) was performed, Compound 6 showed dose dependent increases KYN (see FIG. 1), as well as protective metabolites KYNA (see FIG. 2) & AA (see FIG. 3) in mouse striatum, while there was little or no effect on harmful metabolite 3-HK (see FIG. 4).

Example 12

A method of examining the modulation of KP metabolites in HD animals similar to WT controls is disclosed. Specifically, this experiment is aimed at demonstrating that Compound 6 modulates the differences in KYNA elevations in an animal brain. Following the microdialysis procedure described herein, dialysate levels of KP metabolite KYNA was quantified by LC-MS/MS at by Brains On-Line.

Figure 5:
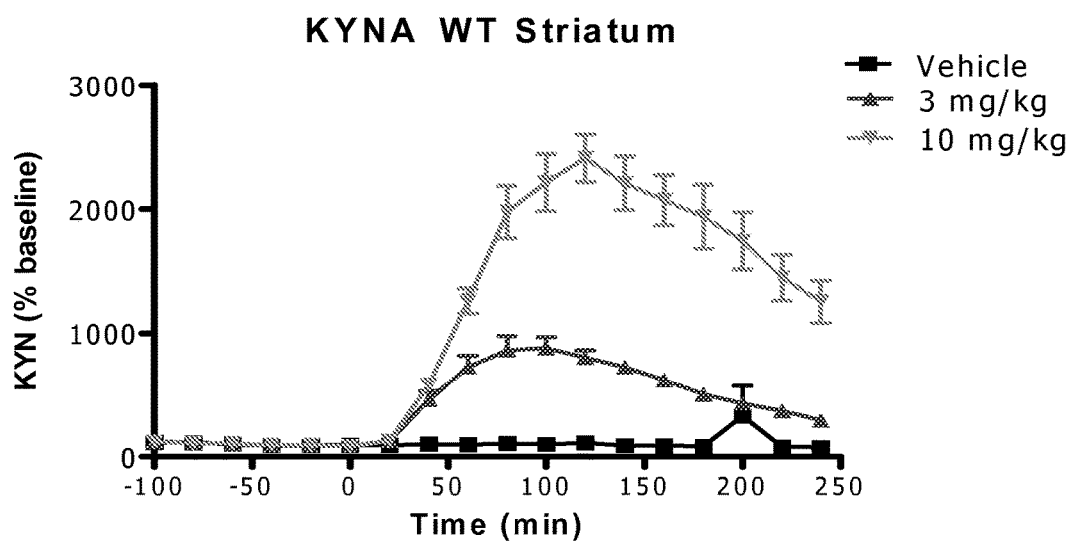
FIG. 5. shows the dose dependent increase of kynurenine pathway (KP) metabolites in the striatum following dosing of Compound 6 in wild type mice.
Figure 6:
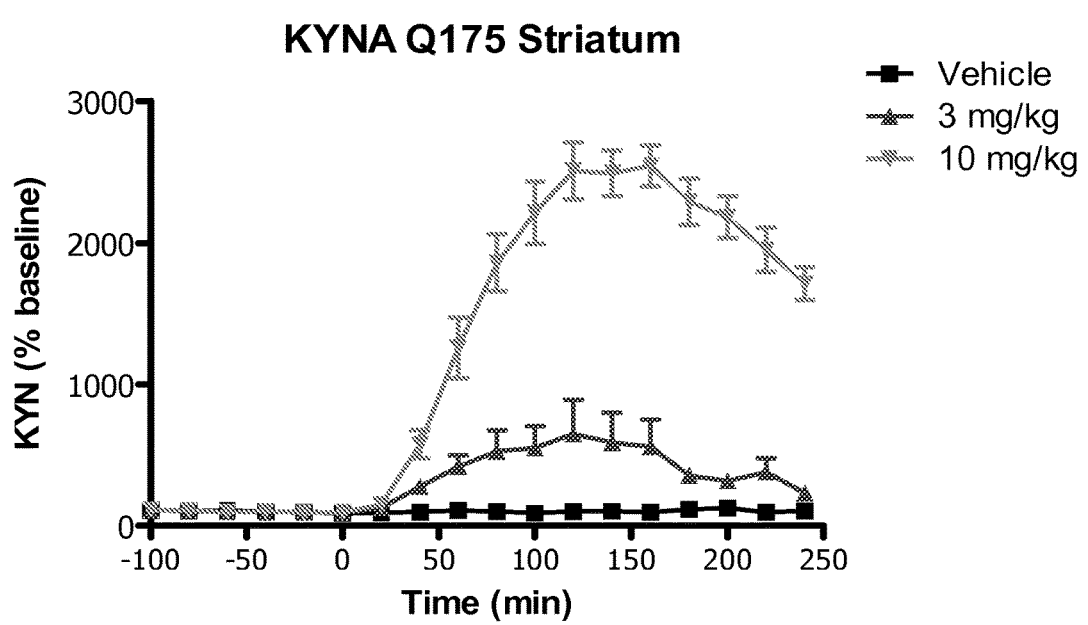
FIG. 6. shows the dose dependent increase of kynurenine pathway metabolites in the striatum following dosing of Compound 6 in Q175_KI homozygous mice.

When microdialysis after PO dosing of Compound 6 at either 3 mg/kg or 10 mg/kg was performed, it was shown that Compound 6 increases KYNA in both WT (see FIG. 5) and HD animals (see FIG. 6), with little difference between the two.

Example 13

A method of examining the pharmacodynamic effects of kynurenine (30 mg/kg, p.o.) and Compound 6 (30 mg/kg, p.o.) on extracellular levels of KYN, KYNA, 3-OH—KYN, AA and QA in the striatum (STR) of adult male WT mice either co-dosed or dosed independently is disclosed. Specifically, this experiment is aimed at demonstrating the differences in central KP metabolite elevations between Kynurenine dosing versus dosing a KMO inhibitor expected to block kynurenine catabolism downstream of KMO in an animal brain.

Figure 7:
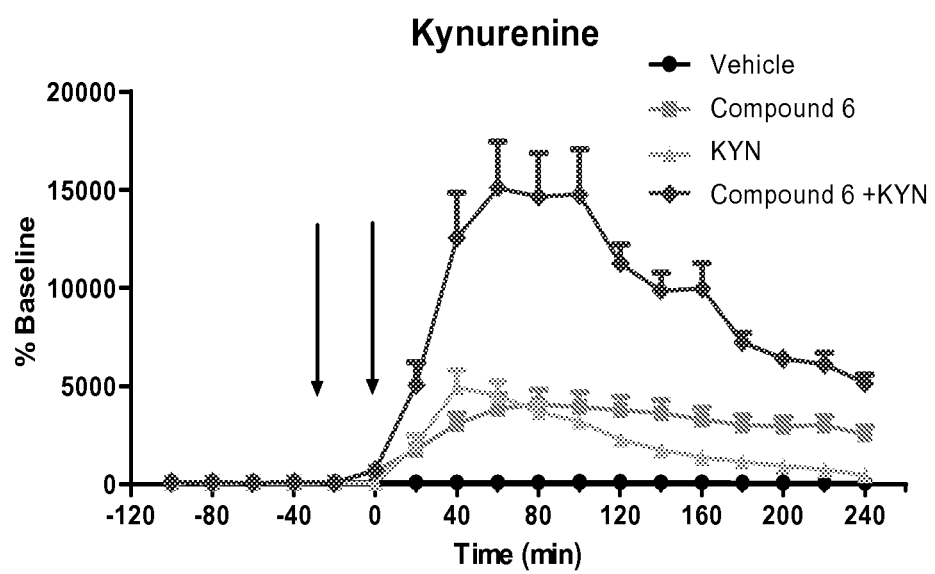
FIG. 7. shows the modulation of KYN in the striatum following dosing of Compound 6, KYN, and (Compound 6+KYN).
Figure 8:
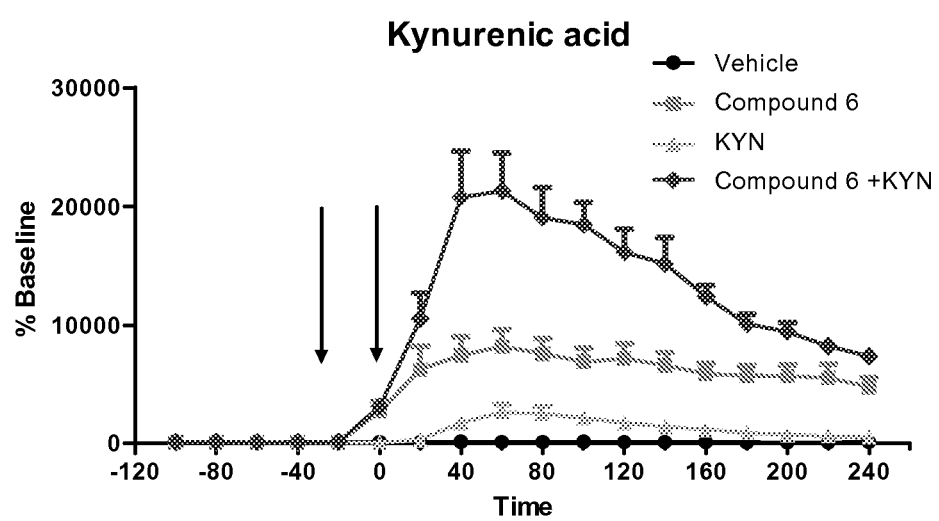
FIG. 8. shows the modulation of KYNA in the striatum following dosing of Compound 6, KYN, and (Compound 6+KYN).
Figure 9:
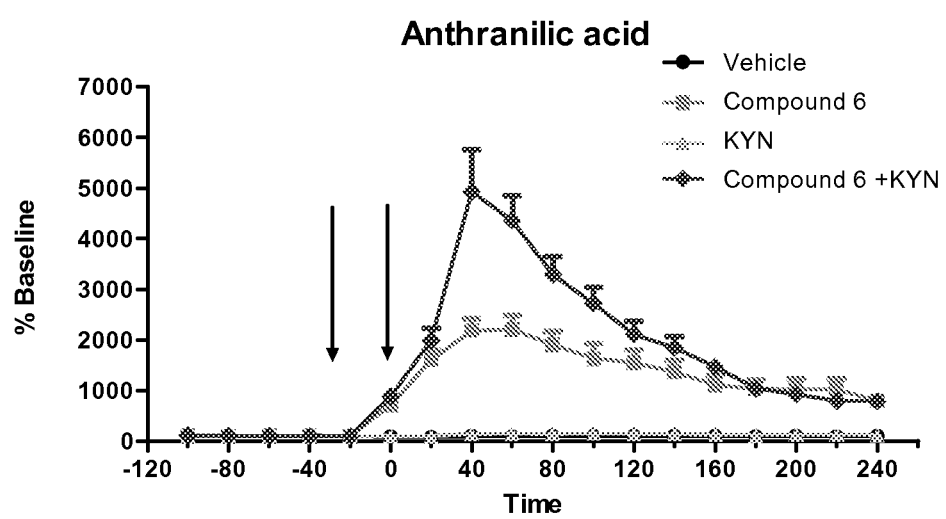
FIG. 9. shows the modulation of anthranilic acid (AA) in the striatum following dosing of Compound 6, KYN, and (Compound 6+KYN).
Figure 10:
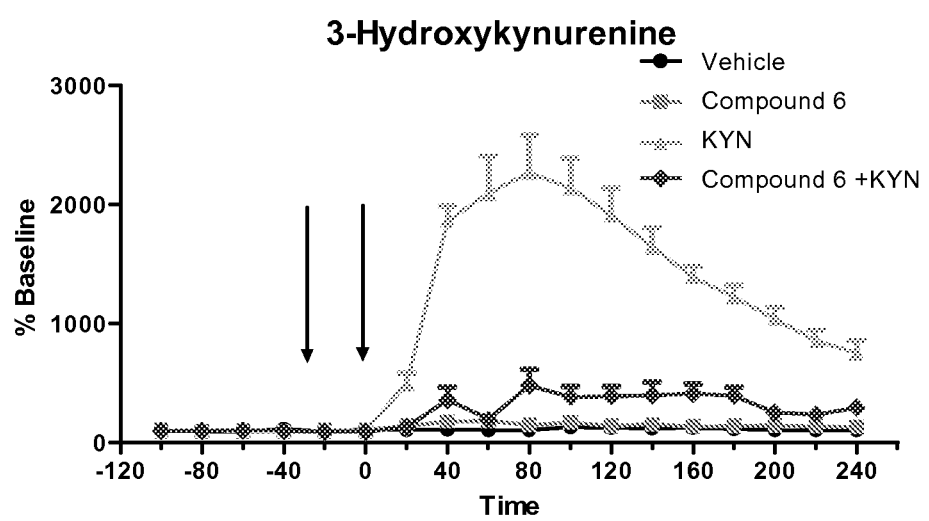
FIG. 10. shows the modulation of 3-OH—KYN in the striatum following dosing of Compound 6, KYN, and (Compound 6+KYN).
Figure 11:
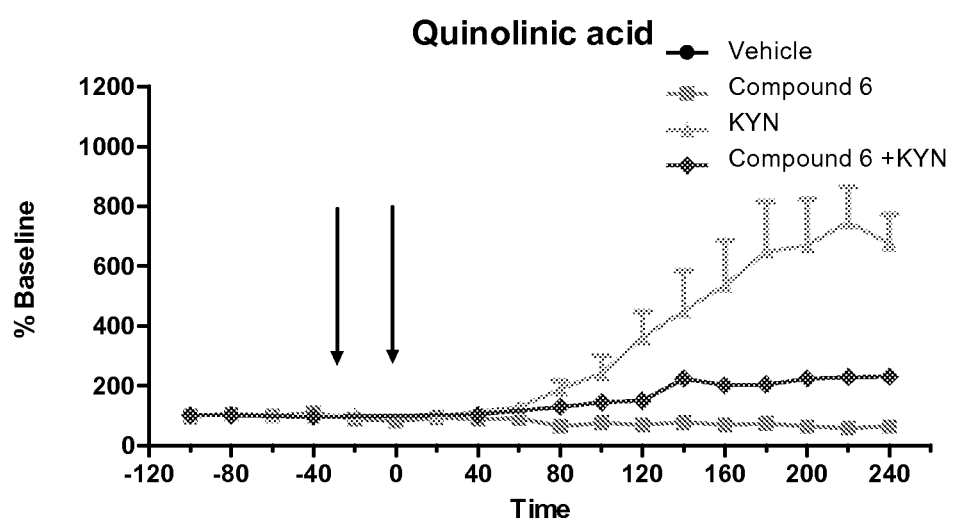
FIG. 11. shows the modulation of quinolinic acid (QA) in the striatum following dosing of Compound 6, KYN, and (Compound 6+KYN).

When microdialysis after PO dosing of kynurenine (30 mg/kg, p.o.), Compound 6 (30 mg/kg, p.o.), or kynurenine and Compound 6 co-dosed (30 mg/kg, p.o. each) was performed, it was shown that Compound 6 increases KYN (see FIG. 7), as well as protective metabolites KYNA (see FIG. 8) & AA (see FIG. 9) in mouse striatum, while kynurenine alone has little or no effect on these metabolites. Furthermore, PO administration of Compound 6 blocks toxic metabolites 3-OH—KYN (see FIG. 10) and QA (see FIG. 11), whereas kynurenine dosing increases them, due to kynurenine catabolism in mice brain.

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A method of treating an HIV-related disorder in a subject infected with HIV, comprising administering to a subject in need thereof a therapeutically effective amount of a compound of formula:

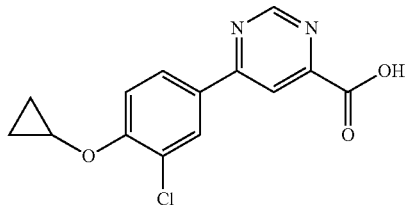 [SMILES: O=C(O)c1cc(-c2ccc(OC3CC3)c(Cl)c2)ncn1]

or a pharmaceutically acceptable salt thereof;
followed by administering to the subject an antiviral agent,
wherein the antiviral agent is selected from emtricitabine, raltegravir, darunavir, tenofovir alafenamide fumarate, emtricitabine/tenofovir, tenofovir disoproxil, and combinations thereof.

2. The method according to claim 1, wherein said compound, or a pharmaceutically acceptable salt thereof, and said antiviral agent are co-packaged in a single container or in a plurality of containers within a single outer package.

3. The method according to claim 1, wherein said HIV is HIV-1.

4. The method according to claim 3, wherein said HIV is HIV-1 group M.

* * * * *